US005420264A

United States Patent [19]

Seed et al.

[11] Patent Number: 5,420,264

[45] Date of Patent: May 30, 1995

[54] NON-HUMAN PRIMATE CD4 POLYPEPTIDES, HUMAN CD4 MOLECULES CAPABLE OF GLYCOSYLATION, FRAGMENTS THEREOF, FUSION PROTEINS THEREOF, GENETIC SEQUENCES THEREOF, AND THE USE THEREOF

[75] Inventors: Brian Seed, Boston, Mass.; David Camerini, Los Angeles, Calif.

[73] Assignee: The General Hospital Corporation, Boston, Mass.

[21] Appl. No.: 914,634

[22] Filed: Jul. 17, 1992

Related U.S. Application Data

[63] Continuation of Ser. No. 397,782, Aug. 23, 1989, abandoned.

[51] Int. Cl.[6] .................... C07H 17/00; C12N 15/00; C12N 5/00; C12N 1/00

[52] U.S. Cl. .................................. 536/23.5; 536/23.1; 536/23.4; 536/23.53; 935/1; 935/11; 935/22; 435/320.1; 435/240.1; 435/243; 435/240.2; 435/252.3

[58] Field of Search ..................... 435/5, 252.31, 69.1, 435/91, 974, 320.1, 240.1, 243, 240.2, 253.3, 252.3; 536/23.7, 23.1, 23.5, 23.53, 23.72, 23.4; 930/220; 935/22.1, 11

[56] References Cited

U.S. PATENT DOCUMENTS

| | | | |
|---|---|---|---|
| 4,675,382 | 6/1987 | Murphy . | |
| 4,816,397 | 3/1989 | Boss et al. | 435/252.31 |
| 4,816,567 | 3/1989 | Cabilly et al. . | |
| 4,935,496 | 6/1990 | Kudo et al. . | |

FOREIGN PATENT DOCUMENTS

| | | |
|---|---|---|
| 0120694 | 10/1984 | European Pat. Off. . |
| 0125023 | 11/1984 | European Pat. Off. . |
| 0314317 | 3/1989 | European Pat. Off. . |
| 0341444 | 11/1989 | European Pat. Off. . |
| WO88/01304 | 2/1988 | WIPO . |
| WO89/01940 | 3/1989 | WIPO . |
| WO89/02922 | 4/1989 | WIPO . |
| WO89/03222 | 4/1989 | WIPO . |
| 18903222 | 4/1989 | WIPO . |
| 8902922 | 6/1989 | WIPO . |
| WO89/06690 | 7/1989 | WIPO . |

OTHER PUBLICATIONS

Fisher, *Nature* 331:76–78 (1988).
Deen, *Nature* 331:82–84 (1988).
Seed et al., *Proc. Natl. Acad. Sci. (USA)* 84:3365–3369 (1987).
Peterson et al., *Cell* 54:65–72 (1988).
Hussey, et al., *Nature* 331:78–81 (1988).
Rusche, J. A. et al., *Proc. Natl. Acad. Sci. (USA)* 85:3198–3202 (1988).
Boulianne, G. L. et al., *Nature* 312:643–646 (1984).
Morrison, S. L. et al., *Proc. Natl. Acad. Sci. (USA)* 81:6851–6855 (1984).
Palker, T. J. et al., *Proc. Natl. Acad. Sci. (USA)* 84:2479–2483 (1987).
Neuberger, M. S. et al., *Nature* 312:604–608 (1984).
Capon, D. J. et al., *Nature* 337:525–531 (1989).
Smith, D. H. et al., *Science* 238:1704–1707 (1987).
Estess, P. et al., *J. Cell. Biochem.* (Suppl. 11D): Abstract 331, p. 258 (1987).
Clark, S. et al., *Proc. Natl. Acad. Sci. (USA)* 84:1649 (1987).
Maddon, P. J. et al., *Cell* 42:93–104 (1985).
Kowalski, M. et al., *Science* 237:1351–1355 (1987).
Stricker, R. B. et al., *Nature* 327:710–713 (1987).

(List continued on next page.)

*Primary Examiner*—Margaret Moskowitz Parr
*Assistant Examiner*—Bradley L. Sisson
*Attorney, Agent, or Firm*—Sterne, Kessler, Goldstein & Fox

[57] ABSTRACT

The present invention relates, in general, to substantially pure polynucleotide molecules specifying chimpanzee or rhesus monkey CD4, and fragments thereof and Gp120 binding molecules related to human CD4. The present invention further relates to polynucleotide molecules specifying CD4 fusion proteins and host cells containing the polynucleotide molecules.

7 Claims, No Drawings

OTHER PUBLICATIONS

Gascoigne, N. R. J. et al., *Proc. Natl. Acad. Sci. (USA)* 84:2936–2940 (1987).
Traunecker, A. et al., *Nature* 331:84–86 (1988).
Lasky, L. A. et al., *Cell* 50:975–985 (1987).
Fisher, et al. *Nature* vol. 331, 7 Jan. 1988.
McDougal et al., "Binding of HTLV-III/LAV to T4+ T Cells by a Complex of the 110K Viral Protein and the T4 Molecule", *Science* 231:382–385 (1986).
Smith et al., "Blocking of HIV-1 Infectivity by a Soluble, Secreted Form of the CD4 Antigen", *Science* 238:1704–1707 (1987).
Mizukami et al., "Expression and Characterization of Chimeric Proteins Containing Human CD4 Linked to Human Immunoglobulin Heavy Chain Constant Regions", Abstract No. M.C.P. 89 (1989).
Sequence Comparison, "5. PANDY-914034 (1–1374)".
Sequence Comparison, "2. SEQ ID 3 (1–1374)".
Sequence Comparison, "3. SEQ ID 4 (1–402)".
Sequence Comparison, "2. SEQ ID 5 (1–1374)".
Sequence Comparison, "2. SEQ ID 6 (1–1377)".
Sequence Comparison, "5. SEQ ID 7 (1–402)".
Arthur, et al., *P.N.A.S. U.S.A.*, vol. 84, pp. 8583–8587, Dec. 1987.
Ward, et al., *Am J Pathol.* 127(2). 1987. abstract only.
Sequence Comparison "10. PANDY-914634 (1–1374)".
Camerini and Seed, *Cell*, vol. 60, pp. 747–754, Mar. 9, 1990.

NON-HUMAN PRIMATE CD4 POLYPEPTIDES, HUMAN CD4 MOLECULES CAPABLE OF GLYCOSYLATION, FRAGMENTS THEREOF, FUSION PROTEINS THEREOF, GENETIC SEQUENCES THEREOF, AND THE USE THEREOF

This application is a continuation of application Ser. No. 07/397,782, filed Aug. 23, 1989, abandoned.

FIELD OF THE INVENTION

The invention is in the field of recombinant genetics and pharmaceutical compositions.

BACKGROUND OF THE INVENTION

The human and simian immunodeficiency viruses HIV and SIV are the causative agents of Acquired Immune Deficiency Syndrome (AIDS) and Simian Immunodeficiency Syndrome (SIDS), respectively. See Curren, J. et al., *Science* 329:1359–1357 (1985); Weiss, R. et al., *Nature* 324:572–575 (1986). The HIV virus contains an envelope glycoprotein, gp120 which binds to the CD4 protein present on the surface of helper T lymphocytes, macrophages and other cells. Dalgleish et al. *Nature*, 312:763 (1984). After the gp120 binds to CD4, virus entry is facilitated by an envelope-mediated fusion of the vital target cell membranes.

During the course of infection, the host organism develops antibodies against viral proteins, including the major envelope glycoproteins gp120 and gp41. Despite this humoral immunity, the disease progresses, resulting in a lethal immunosuppression characterized by multiple opportunistic infections, parasitemia, dementia and death. The failure of host anti-viral antibodies to arrest the progression of the disease represents one of the most vexing and alarming aspects of the infection, and augurs poorly for vaccination efforts based upon conventional approaches.

Two factors may play a role in the inefficacy of the humoral response to immunodeficiency viruses. First, like other RNA viruses (and like retroviruses in particular), the immunodeficiency viruses show a high mutation rate which allows antigenic variation to progress at a high rate in response to host immune surveillance. Second, the envelope glycoproteins themselves are heavily glycosylated molecules presenting few epitopes suitable for high affinity antibody binding. The poorly antigenic, "moving" target which the viral envelope presents, allows the host little opportunity for restricting viral infection by specific antibody production.

Cells infected by the HIV virus express the gp120 glycoprotein on their surface. Gp120 mediates fusion events among CD4+ cells via a reaction similar to that by which the virus enters the uninfected cell, leading to the formation of short-lived multinucleated giant cells. Syncytium formation is dependent on a direct interaction of the gp120 envelope glycoprotein with the CD4 protein. Dalgleish et al., supra, Klatzmann, D. et al., Nature 312:763 (1984); McDougal, J. S. et al. *Science*, 231:382 (1986); Sodroski, J. et al., *Nature*, 322:470 (1986); Lifson, J. D. et al., *Nature*, 323:725 (1986); Sodroski, J. et al., *Nature*, 321:412 (1986).

The human CD4 protein consists of a 372 amino acid extracellular region containing four immunoglobulin-like domains, a membrane spanning domain, and a charged intracellular region of 40 amino acid residues.

Maddon, P. et al., *Cell* 42:93 (1985); Clark, S. et al., *Proc. Natl. Acad. Sci.* (USA) 84:1649 (1987).

Evidence that CD4-gp120 binding is responsible for viral infection of cells bearing the CD4 antigen includes the finding that a specific complex is formed between gp120 and CD4. McDougal et al., supra. Other workers have shown that cell lines, which were non-infective for HIV, were converted to infectable cell lines following transfection and expression of the human CD4 cDNA gene. Maddon et al., *Cell* 47:333–348 (1986). PCT Application Publication Nos. WO 88/01304 (1988) and W089/01940 (1989) disclose that soluble forms of human CD4 comprising the immunoglobulin-like binding domains are useful for the treatment or prophylaxis of HIV infections.

In contrast to the majority of antibody-envelope interactions, the receptor-envelope interaction is characterized by a high affinity ($K_a \approx 10^8$l/mole) immutable association. Moreover, the affinity of the virus for human CD4 is at least 3 orders of magnitude higher than the affinity of human CD4 for its putative endogenous ligand, the MHC class II antigens.

A number of workers have disclosed methods for preparing hybrid proteins. For example, Murphy, U.S. Pat. No. 4,675,382 (1987), discloses the use of recombinant DNA techniques to make hybrid protein molecules by forming the desired fused gene coding for a hybrid protein of diphtheria toxin and a polypeptide ligand such as a hormone, followed by expression of the fused gene.

Many workers have prepared monoclonal antibodies (Mabs) by recombinant DNA techniques. Monoclonal antibodies are highly specific well-characterized molecules in both primary and tertiary structure. They have been widely used for in vitro immunochemical characterization and quantitation of antigens. Genes for heavy and light chains have been introduced into appropriate hosts and expressed, followed by reaggregation of the individual chains into functional antibody molecules (see, for example, Munro, *Nature* 312:597 (1984); Morrison, S. L., *Science* 229:1202 (1985); Oi et al., *Biotechniques* 4:214 (1986); Wood et al., *Nature* 314:446–449 (1985)). Light- and heavy-chain variable regions have been cloned and expressed in foreign hosts wherein they maintained their binding ability (Moore et al., European Patent Application 0088994 (published Sep. 21, 1983)).

Chimeric or hybrid antibodies have also been prepared by recombinant DNA techniques. Oi and Morrison, *Biotechniques* 4:214 (1986) describe a strategy for producing such chimeric antibodies which include a chimeric human IgG anti-leu3 antibody.

Gascoigne, N. R. J., et al., *Proc. Natl. Acad. Sci.* (USA) 84:2936–2940 (1987) disclose the preparation of a chimeric gene construct containing a T-cell receptor α-chain variable (V) domain and the constant (C) region coding sequence of an immunoglobulin $_{\gamma}$2a molecule. Cells transfected with the chimeric gene synthesize a protein product that expresses immunoglobulin and T-cell receptor antigenic determinants as well as protein A binding sites. This protein associates with a normal λ chain to form an apparently normal tetrameric ($H_2L_2$, where H=heavy and L=light) immunoglobulin molecule that is secreted.

Sharon, J., et al., *Nature* 309:54 (1984), disclose construction of a chimeric gene encoding the variable (V) region of a mouse heavy chain specific for the hapten azophenylarsonate and the constant (C) region of a mouse kappa light chain ($V_HC_K$). This gene was introduced into a mouse myeloma cell line. The chimeric gene was expressed to give a protein which associated with light chains secreted from the myeloma cell line to give an antibody molecule specific for azophenylarsonate.

Morrison, *Science* 229:1202 (1985), discloses that variable light- or variable heavy-chain regions can be attached to a non-Ig sequence to create fusion proteins. This article states that the potential uses for the fusion proteins are three: (1) to attach antibody specifically to enzymes for use in assays; (2) to isolate non-Ig proteins by antigen columns; and (3) to specifically deliver toxic agents.

Recent techniques for the stable introduction of immunoglobulin genes into myeloma cells (Banerji, J., et al., *Cell* 33:729–740 (1983); Potter, H., et al., *Proc. Natl. Acad. Sci.* (USA) 81:7161–7165 (1984)), coupled with detailed structural information, have permitted the use of in vitro DNA methods such as mutagenesis, to generate recombinant antibodies possessing novel properties.

PCT Application WO87/02671 discloses methods for producing genetically engineered antibodies of desired variable region specificity and constant region properties through gene cloning and expression of light and heavy chains. The mRNA from cloned hybridoma B cell lines which produce monoclonal antibodies of desired specificity is isolated for cDNA cloning. The generation of light and heavy chain coding sequences is accomplished by excising the cloned variable regions and ligating them to light or heavy chain module vectors. This gives cDNA sequences which code for immunoglobulin chains. The lack of introns allows these cDNA sequences to be expressed in prokaryotic hosts, such as bacteria, or in lower eukaryotic hosts, such as yeast.

The generation of chimeric antibodies in which the antigen-binding portion of the immunoglobulin is fused to other moieties has been demonstrated. Examples of non-immunoglobulin genes fused to antibodies include *Staphylococcus aureus* nuclease, the mouse oncogene c-myc, and the Klenow fragment of *E. coli* DNA polymerase I (Neuberger, M. S., et al., *Nature* 312:604–612 (1984); Neuberger, M. S., *Trends in Biochemical Science,* 347–349 (1985)). European Patent Application 120,694 discloses the genetic engineering of the variable and constant regions of an immunoglobulin molecule that is expressed in *E. coli* host cells. It is further disclosed that the immunoglobulin molecule may be synthesized by a host cell with another peptide moiety attached to one of the constant domains. Such peptide moieties are described as either cytotoxic or enzymatic. The application and the examples describe the use of a lambda-like chain derived from a monoclonal antibody which binds to 4-hydroxy-3-nitrophenyl (NP) haptens.

European Patent Application 125,023 relates to the use of recombinant DNA techniques to produce immunoglobulin molecules that are chimeric or otherwise modified. One of the uses described for these immunoglobulin molecules is for whole-body diagnosis and treatment by injection of the antibodies directed to specific target tissues. The presence of the disease can be determined by attaching a suitable label to the antibodies, or the diseased tissue can be attacked by carrying a suitable drug with the antibodies. The application describes antibodies engineered to aid the specific delivery of an agent as "altered antibodies."

PCT Application WO83/101533 describes chimeric antibodies wherein the variable region of an immunoglobulin molecule is linked to a portion of a second protein which may comprise the active portion of an enzyme.

Boulianne et al., *Nature* 312:643 (1984) constructed an immunoglobulin gene in which the DNA segments that encode mouse variable regions specific for the hapten trinitrophenol (TNP) are joined to segments that encode human mu and kappa regions. These chimeric genes were expressed to give functional TNP-binding chimeric IgM.

Morrison et al., *P.N.A.S.* (USA) 81:6851 (1984), disclose a chimeric molecule utilizing the heavy-chain variable region exons of an anti-phosphoryl choline myeloma protein G, which were joined to the exons of either human kappa light-chain gene. The genes were transfected into mouse myeloma cell lines, generating transformed cells that produced chimeric mouse-human IgG with antigen-binding function.

PCT Application Publication No. WO89/02922 (1989), discloses chimeric antibody molecules comprising human CD4. Such chimeric antibody molecules may be administered to a subject infected with HIV to treat the HIV infection.

Despite the progress that has been achieved on determining the mechanism of HIV infection, a need continues to exist for methods of treating HIV viral infections.

SUMMARY OF THE INVENTION

The invention relates to a nucleic acid molecule specifying non-human primate CD4, or an HIV or SIV gp120 binding fragment thereof.

In particular, the invention relates to a nucleic acid molecule specifying rhesus monkey CD4 comprising the following DNA sequence:

```
  1 ATGAACCGGGGAATCCCTTTTAGGCACTTGCTTCTGGTGCTGCAACTGGCGCTACTCCCA
-25 Met Asn Arg Gly Ile Pro Phe Arg His Leu Leu Leu Val Leu Gln Leu Ala Leu Leu Pro

    GCAGTCACCCAGGGAAAGAAAGTGGTGCTGGGCAAGAAAGGGGATACAGTGGAACTGACC 120
    Ala Val Thr Gln Gly Lys Lys Val Val Leu Gly Lys Lys Gly Asp Thr Val Glu Leu Thr 15

121 TGTACAGCTTCGCAGAAGAAGAACACACAATTCCACTGGAAAAACTCCAACCAGATAAAG
 16 Cys Thr Ala Ser Gln Lys Lys Asn Thr Gln Phe His Trp Lys Asn Ser Asn Gln Ile Lys

    ATTCTGGGAATTCAGGGTCTCTTCTTAACTAAAGGTCCATCCAAGCTGAGCGATCGTGCT 240
    Ile Leu Gly Ile Gln Gly Leu Phe Leu Thr Lys Gly Pro Ser Lys Leu Ser Asp Arg Ala 55

241 GACTCAAGAAAAAGCCTTTGGGACCAAGGATGCTTTTCCATGATCATCAATAATCTTAAG
 56 Asp Ser Arg Lys Ser Leu Trp Asp Gln Gly Cys Phe Ser Met Ile Ile Lys Asn Leu Lys
```

-continued

ATAGAAGACTCAGATACTTACATCTGTGAAGTGGAGAACAAGAAGGAGGAGGTGGAATTG 360
Ile Glu Asp Ser Asp Thr Tyr Ile Cys Glu Val Glu Asn Lys Lys Glu Glu Val Glu Leu 95

361 CTGGTGTTCGGATTGACTGCCAACTCTGACACCCACCTGCTTGAGGGGCAAAGCCTGACC
96 Leu Val Phe Gly Leu Thr Ala Asn Ser Asp Thr His Leu Leu Glu Gly Gln Ser Leu Thr

CTGACCTTGGAGAGCCCCCCTGGTAGTAGCCCCTCAGTGAAATGTAGGAGTCCAGGGGGT 480
Leu Thr Leu Glu Ser Pro Pro Gly Ser Ser Pro Ser Val Lys Cys Arg Ser Pro Gly Gly 135

481 AAAAACATACAGGGGGGGAGGACCATCTCTGTGCCTCAGCTGGAGCGCCAGGATAGTGGC
136 Lys Asn Ile Gln Gly Gly Arg Thr Ile Ser Val Pro Gln Leu Glu Arg Gln Asp Ser Gly

ACCTGGACATGCACCGTCTCGCAGGACCAGAAGACGGTGGAGTTCAAAATAGACATCGTG 600
Thr Trp Thr Cys Thr Val Ser Gln Asp Gln Lys Thr Val Glu Phe Lys Ile Asp Ile Val 175

601 GTGCTAGCTTTCCAGAAGGCCTCCAGCACAGTCTATAAGAAAGAGGGGGAACAGGTGGAG
176 Val Leu Ala Phe Gln Lys Ala Ser Ser Thr Val Tyr Lys Lys Glu Gly Glu Gln Val Glu

TTCTCCTTCCCACTCGCCTTTACACTTGAAAAGCTGACGGGCAGTGGCGAGCTGTGGTGG 720
Phe Ser Phe Pro Leu Ala Phe Thr Leu Glu Lys Leu Thr Gly Ser Gly Glu Leu Trp Trp 215

721 CAGGCGGAGAGGGCCTCCTCCTCCAAGTCTTGGATTACCTTCGACCTGAAGAACAAGGAA
216 Gln Ala Glu Arg Ala Ser Ser Ser Lys Ser Trp Ile Thr Phe Asp Leu Lys Asn Lys Glu

GTGTCTGTAAAACGGGTTACCCAGGACCCCAAGCTCCAGATGGGCAAGAAGCTCCCGCTC 840
Val Ser Val Lys Arg Val Thr Gln Asp Pro Lys Leu Gln Met Gly Lys Lys Leu Pro Leu 255

841 CACCTCACCCTGCCCCAGGCCTTGCCTCAGTATGCTGGCTCTGGAAACCTCACGCTGGCC
256 His Leu Thr Leu Pro Gln Ala Leu Pro Gln Tyr Ala Gly Ser Gly Asn Leu Thr Leu Ala

CTTGAAGCGAAAACAGGAAAGTTGCATCAGGAAGTGAACCTCGTGGTGATGAGAGCCACT 960
Leu Glu Ala Lys Thr Gly Lys Leu His Gln Glu Val Asn Leu Val Val Met Arg Ala Thr 295

961 CAGTTCCAGGAAAATTTGACCTGTGAAGTGTGGGGACCCACCTCCCCTAAGCTGACGCTG
296 Gln Phe Gln Glu Asn Leu Thr Cys Glu Val Trp Gly Pro Thr Ser Pro Lys Leu Thr Leu

AGCTTGAAACTGGAGAACAAGGGGGCAACGGTCTCGAAGCAGGCGAAGGCGGTGTGGGTG 1080
Ser Leu Lys Leu Glu Asn Lys Gly Ala Thr Val Ser Lys Gln Ala Lys Ala Val Trp Val 335

1081 CTGAACCCTGAGGCGGGGATGTGGCAGTGTCTGCTGAGTGACTCGGGACAGGTCCTGCTA
336 Leu Asn Pro Glu Ala Gly Met Trp Gln Cys Leu Leu Ser Asp Ser Gly Gln Val Leu Leu

GAATCCAACATCAAGGTTGTGCCCACATGGCCCACCCCGGTGCAGCCAATGGCCCTGATT 1200
Glu Ser Asn Ile Lys Val Val Pro Thr Trp Pro Thr Pro Val Gln Pro Met Ala Leu Ile 375

1201 GTGCTGGGGGGCGTTGCGGGCCTCCTGCTTTTCACTGGGCTAGGCATCTTCTTCTGTGTC
376 Val Leu Gly Gly Val Ala Gly Leu Leu Leu Phe Thr Gly Leu Gly Ile Phe Phe Cys Val

AGGTGCCGGCATCGAAGGCGTCAAGCAGAGCGGATGTCTCAGATCAAGAGACTCCTCAGT 1320
Arg Cys Arg His Arg Arg Arg Gln Ala Glu Arg Met Ser Gln Ile Lys Arg Leu Leu Ser 415

1321 GAAAAGAAGACCTGCCAGTGCCCTCACCGGTTTCAGAAGACATGTAGCCCCATTTGA 1377
416 Glu Lys Lys Thr Cys Gln Cys Pro His Arg Phe Gln Lys Thr Cys Ser Pro Ile End 433 or a degenerate variant thereof.

The invention also relates to a nucleic acid molecule specifying a soluble non-human primate CD4 fragment.

In particular, the invention to a soluble rhesus CD4 fragment (domain I) which binds HIV or SIV gp120 comprising the following DNA sequence:

1 ATGAACCGGGGAATCCCTTTTAGGCACTTGCTTCTGGTGCTGCAACTGGCGCTACTCCCA
−25 Met Asn Arg Gly Ile Pro Phe Arg His Leu Leu Leu Val Leu Gln Leu Ala Leu Leu Pro

-continued

```
    GCAGTCACCCAGGGAAAGAAAGTGGTGCTGGGCAAGAAAGGGGATACAGTGGAACTGACC 120
    Ala Val Thr Gln Gly Lys Lys Val Val Leu Gly Lys Lys Gly Asp Thr Val Glu Leu Thr 15

121 TGTACAGCTTCGCAGAAGAAGAACACACAATTCCACTGGAAAAACTCCAACCAGATAAAG
 16 Cys Thr Ala Ser Gln Lys Lys Asn Thr Gln Phe His Trp Lys Asn Ser Asn Gln Ile Lys

    ATTCTGGGAATTCAGGGTCTCTTCTTAACTAAAGGTCCATCCAAGCTGAGCGATCGTGCT 240
    Ile Leu Gly Ile Gln Gly Leu Phe Leu Thr Lys Gly Pro Ser Lys Leu Ser Asp Arg Ala 55

241 GACTCAAGAAAAAGCCTTTGGGACCAAGGATGCTTTTCCATGATCATCAAGAATCTTAAG
 56 Asp Ser Arg Lys Ser Leu Trp Asp Gln Gly Cys Phe Ser Met Ile Ile Lys Asn Leu Lys

    ATAGAAGACTCAGATACTTACATCTGTGAAGTGGAGAACAAGAAGGAGGAGGTGGAATTG 360
    Ile Glu Asp Ser Asp Thr Tyr Ile Cys Glu Val Glu Asn Lys Lys Glu Glu Val Glu Leu 95

361 CTGGTGTTCGGATTGACTGCCAACTCTGACACCCACCTGCTT
 96 Leu Val Phe Gly Leu Thr Ala Asn Ser Asp Thr His Leu Leu
```

or a degenerate variant thereof.

The invention also relates to a nucleic acid molecule specifying chimpanzee CD4, comprising the following DNA sequence:

```
  1 ATGAACCGGGGAGTCCCTTTTAGGCACTTGCTTCTGGTGCTGCAACTGGCACTCCTCCCA
-25 Met Asn Arg Gly Ile Pro Phe Arg His Leu Leu Leu Val Leu Gln Leu Ala Leu Leu Pro

    GCAGCCACTCAGGGAAAGAAAGTGGTGCTGGGCAAGAAAGGGGACACAGTGGAACTGACC 120
    Ala Ala Thr Gln Gly Lys Lys Val Val Leu Gly Lys Lys Gly Asp Thr Val Glu Leu Thr 15

121 TGTACAGCTTCCCAGAAGAAGAGCATACAATTCCACTGGAAAAACTCCAACCAGACAAAG
 16 Cys Thr Ala Ser Gln Lys Lys Ser Ile Gln Phe His Trp Lys Asn Ser Asn Gln Ile Lys

    ATTCTGGGAAATCAGGGCTCCTTCTTAACTAAAGGTCCATCCAAGCTGAATGATCGCGTT 240
    Ile Leu Gly Ile Gln Gly Leu Phe Leu Thr Lys Gly Pro Ser Lys Leu Ser Asp Arg Val 55

241 GACTCAAGAAGAAGCCTTTGGGACCAAGGAAACTTTACCCTGATCATCAAG AATCTTAAG
 56 Asp Ser Arg Arg Ser Leu Trp Asp Gln Gly Asn Phe Thr Leu Ile Ile Lys Asn Leu Lys

    ATAGAAGACTCAGATACTTACATCTGTGAAGTGGGGGACCAGAAGGAGGAGGTGCAATTG 360
    Ile Glu Asp Ser Asp Thr Tyr Ile Cys Glu Val Gly Asp Lys Lys Glu Glu Val Glu Leu 95

361 CTAGTGTTCGGATTGACTGCCAACTCTGACACCCACCTGCTTCAGGGGCAGAGCCTGACC
 96 Leu Val Phe Gly Leu Thr Ala Asn Ser Asp Thr His Leu Leu Gln Gly Gln Ser Leu Thr

    CTGACCTTGGAGAGCCCCCCTGGTAGTAGCCCCTCAGTGCAATGTAGGAGTCCAAGGGGT 360
    Leu Thr Leu Glu Ser Pro Pro Gly Ser Ser Pro Ser Val Gln Cys Arg Ser Pro Arg Gly 135

481 AAAAACATACAGGGGGGGAAGACCCTCTCCGTGTCTCAGCTGGAGCTCCAGGATAGTGGC
136 Lys Asn Ile Gln Gly Gly Lys Thr Leu Ser Val Ser Gln Leu Glu Leu Gln Asp Ser Gly

    ACCTGGACATGCACCGTCTTGCAGAACCAGAAGAAAGTGGAGTTCAAAATAGACATCGTG 600
    Thr Trp Thr Cys Thr Val Leu Gln Asn Gln Lys Lys Val Glu Phe Lys Ile Asp Ile Val 175

601 GTGCTAGCTTTCCAGAAGGCCTCCAGCATAGTCTATAAGAAAGAGGGGGAACAGGTGGAG
176 Val Leu Ala Phe Gln Lys Ala Ser Ser Ile Val Tyr Lys Lys Glu Gly Glu Gln Val Glu

    TTCTCCTTCCCACTCGCCTTTACAGTTGAAAAGCTGACGGGCAGTGGCGAGCTGTGGTGG 720
    Phe Ser Phe Pro Leu Ala Phe Thr Val Glu Lys Leu Thr Gly Ser Gly Glu Leu Trp Trp 215

721 CAGGCGGAGAGGGCTTCCTCCTCCAAGTCTTGGATCACCTTTGACCTGAAGAACAAGGAA
216 Gln Ala Glu Arg Ala Ser Ser Ser Lys Ser Trp Ile Thr Phe Asp Leu Lys Asn Lys Glu
```

-continued

GT GT CT GT AAAACGGGT TACCCAGGACCCT AAGCT CCAGAT GGGCAAGAAGCT CCCGCT C 840
Val Ser Val Lys Arg Val Thr Gln Asp Pro Lys Leu Gln Met Gly Lys Lys Leu Pro Leu 255

841 CACCT CACCCT GCCCCAGGCCT T GCCT CAGT AT GCT GGCT CT GGAAACCT CACCCT GGCC
256 His Leu Thr Leu Pro Gln Ala Leu Pro Gln Tyr Ala Gly Ser Gly Asn Leu Thr Leu Ala

CT T GAAGCGAAAACAGGAAAGT T GCAT CAGGAAGT GAACCT CGT GGT GAT GAGAGCCACT 840
Leu Glu Ala Lys Thr Gly Lys Leu His Gln Glu Val Asn Leu Val Val Met Arg Ala Thr 295

961 CAGCT CCAGAAAAAT T T GACCT GT GAGGT GT GGGGACCCACCT CCCCT AAGCT GACGCT G
296 Gln Leu Gln Lys Asn Leu Thr Cys Glu Val Trp Gly Pro Thr Ser Pro Lys Leu Met Leu

AGCT T GAAACT GGAGAACAAGGAGGCAAAGGT CT CGAAGCGGGAGAAGGCGGT GT GGGT G 1080
Ser Leu Lys Leu Glu Asn Lys Glu Ala Lys Val Ser Lys Glu Ala Lys Ala Val Trp Val 335

1081 CT GAACCCT GAGGCGGGGAT GT GGCAGT GT CT GCT GAGT GACT CGGGACAGGT CCT GCT G
336 Leu Asn Pro Glu Ala Gly Met Trp Gln Cys Leu Leu Ser Asp Ser Gly Gln Val Leu Leu

GAAT CCAACAT CAAGGT T CT GCCCACAT GGCCCACCCCGGT GCAGCCAAT GGCCCT GATT 1200
Glu Ser Asn Ile Lys Val Leu Pro Thr Trp Pro Thr Ser Val Gln Pro Met Ala Leu Ile 375

1201 GT GCT GGGGGGCGT GGCCGGCCT CCT GCT T T T CAT T GGGCT AGGCAT CT T CT T CT GT GT C
376 Val Leu Gly Gly Val Ala Gly Leu Leu Leu Phe Ile Gly Leu Gly Ile Phe Phe Cys Val

AGGT GCCGGCACCGAAGGCGCCAAGCACAGCGGAT GT CT CAGAT CAAGAGACT CCT CAGT 1320
Arg Cys Arg His Arg Arg Arg Gln Ala Gln Arg Met Ser Gln Ile Lys Arg Leu Leu Ser 415

1321 GAGAAGAAGACCT GCCAGT GCCCT CACCGGT T T CAGAAGACAT GT AGCCCCAT T T GA 1377
416 Glu Lys Lys Thr Cys Gln Cys Pro His Arg Phe Gln Lys Thr Cys Ser Pro Ile End 433 or a degenerate variant thereof.

The invention also relates to a nucleic acid molecule specifying a soluble chimpanzee CD4 fragment (domain I) which binds HIV or SIV gp120, comprising the following DNA sequence:

1 AT GAACCGGGGAGT CCCT T T T AGGCACT T GCT T CT GGT GCT GCAACT GCAACT GCT CCCA
−25 Met Asn Arg Gly Val Pro Phe Arg His Leu Leu Leu Val Leu Gln Leu Ala Leu Leu Pro

GCAGCCAT CCAGGGAAAGAAAGT GGT GCT GGGCAAGAAAGGGGACACAGT GGAACT GACC 120
Ala Ala Thr Gln Gly Lys Lys Val Val Leu Gly Lys Lys Gly Asp Thr Val Glu Leu Thr 15

121 T GT ACAGCT T CCCAGAAGAAGAGCAT ACAAT T CCACT GGAAAAACT CCAACCAGACAAAG
16 Cys Thr Ala Ser Gln Lys Lys Ser Ile Gln Phe His Trp Lys Asn Ser Asn Gln Thr Lys

AT T CT GGGAAT T CAGGGCT CCT T CT T AACT AAAGGT CCAT CCAAGCT GAAT GAT CGT GT T 240
Ile Leu Gly Asn Gln Gly Ser Phe Leu Thr Lys Gly Pro Ser Lys Leu Asn Asp Arg Val 55

241 GACT CAAGAAGAAGCCT T T GGGACCAAGGAAACT T T ACCCT GAT CAT CAAG AAT CT T AAG
56 Asp Ser Arg Lys Ser Leu Trp Asp Gln Gly Asn Phe Thr Leu Ile Ile Lys Asn Leu Lys

AT AGAAGACT CAGAT ACT T ACAT CT GT GAAGT GGGGGACCAGAAGGAGGAGGT GCAAT T G 360
Ile Glu Asp Ser Asp Thr Tyr Ile Cys Glu Val Gly Asp Gln Lys Glu Glu Val Gln Leu 95

361 CT GGT GT T CGGAT T GACT GCCAACT CT GACACCCACCT GCT T
96 Leu Val Phe Gly Leu Thr Ala Asn Ser Asp Thr His Leu Leu or a degenerate variant thereof.

The invention also relates to a nucleic acid molecule specifying chimpanzee CD4 with the cytoplasmic domain, comprising the following DNA sequence:

1 AT GAACCGGGGAGT CCCT T T T AGGCACT T GCT T CT GGT GCT GCAACT GGCACT CCT CCCA
−25 Met Asn Arg Gly Val Pro Phe Arg His Leu Leu Leu Val Leu Gln Leu Ala Leu Leu Pro

-continued

GCAGCCACTCAGGGAAAGAAAGTGGTGCTGGGCAAGAAAGGGGACACAGTGGAACTGACC 120
Ala Ala Thr Gln Gly Lys Lys Val Val Leu Gly Lys Lys Gly Asp Thr Val Glu Leu Thr 15

121 TGTACAGCTTCCCAGAAGAAGAGCATACAATTCCACTGGAAAAACTCCAACCAGAYAAAG
16 Cys Thr Ala Ser Gln Lys Lys Ser Ile Gln Phe His Trp Lys Asn Ser Asn Gln Thr Lys
Ile

ATTCTGGGAAATCAGGGCTCCTTCTTAACTAAAGGTCCATCCAAGCTGAATGATCGCGYT 240
Ile Leu Gly Asn Gln Gly Ser Phe Leu Thr Lys Gly Pro Ser Lys Leu Asn Asp Arg Val 55
Ala

241 GACTCAAGAAGAAGCCTTTGGGACCAAGGAAACTTTMCCCTGATCATCAAGAATCTTAAG
56 Asp Ser Arg Arg Ser Leu Trp Asp Gln Gly Asn Phe Thr Leu Ile Ile Lys Asn Leu Lys
Pro

ATAGAAGACTCAGATACTTACATCTGTGAAGTGGGGGACCAGAAGGAGGAGGTGCAATTG 360
Ile Glu Asp Ser Asp Thr Tyr Ile Cys Glu Val Gly Asp Gln Lys Glu Glu Val Gln Leu 95

361 CTAGTGTTCGGATTGACTGCCAACTCTGACACCCACCTGCTTCAGGGGCAGAGCCTGACC
96 Leu Val Phe Gly Leu Thr Ala Asn Ser Asp Thr His Leu Leu Gln Gly Gln Ser Leu Thr

CTGACCTTGGAGAGCCCCCCTGGTAGTAGCCCCTCAGTGCAATGTAGGAGTCCAAGGGGT 360
Leu Thr Leu Glu Ser Pro Pro Gly Ser Ser Pro Ser Val Gln Cys Arg Ser Pro Arg Gly 135

481 AAAAACATACAGGGGGGGAAGACCCTCTCCGTGTCTCAGCTGGAGCTCCAGGATAGTGGC
136 Lys Asn Ile Gln Gly Gly Lys Thr Leu Ser Val Ser Gln Leu Glu Leu Gln Asp Ser Gly

ACCTGGACATGCACTGTCTTGCAGAACCAGAAGAAAGTGGAGTTCAAAATAGACATCGTG 600
Thr Trp Thr Cys Thr Val Leu Gln Asn Gln Lys Lys Val Glu Phe Lys Ile Asp Ile Val 175

601 GTGCTAGCTTTCCAGAAGGCCTCCAGCATAGTCTATAAGAAAGAGGGGGAACAGGTGGAG
176 Val Leu Ala Phe Gln Lys Ala Ser Ser Ile Val Tyr Lys Lys Glu Gly Glu Gln Val Glu

TTCTCCTTCCCACTCGCCTTTACAGTTGAAAAGCTGACGGGCAGTGGCGAGCTGTGGTGG 720
Phe Ser Phe Pro Leu Ala Phe Thr Val Glu Lys Leu Thr Gly Ser Gly Glu Leu Trp Trp 215

721 GACGCGGAGAGGGCTTCCTCCTCCAAGTCTTGGATCACCTTTGACCTGAAGAACAAGGAA
216 Gln Ala Glu Arg Ala Ser Ser Ser Lys Ser Trp Ile Thr Phe Asp Leu Lys Asn Lys Glu

GTGTCTGTAAAACGGGTTACCCAGGACCCTAAGCTCCAGATGGGCAAGAAGCTCCCGCTC 840
Val Ser Val Lys Arg Val Thr Gln Asp Pro Lys Leu Gln Met Gly Lys Lys Leu Pro Leu 255

841 CACCTCACCCTGCCCCAGGCCTTGCCTCAGTATGCTGGCTCTGGAAACCTCACCCTGGCC
256 His Leu Thr Leu Pro Gln Ala Leu Pro Gln Tyr Ala Gly Ser Gly Asn Leu Thr Leu Ala

CTTGAAGCGAAAACAGGAAAGTTGCATCAGGAAGTGAACCTCGTGGTGATGAGAGCCACT 840
Leu Glu Ala Lys Thr Gly Lys Leu His Gln Glu Val Asn Leu Val Val Met Arg Ala Thr 295

961 CAGCTCCAGAAAAATTTGACCTGTGAGGTGTGGGGACCCACCTCCCCTAAGCTGATGCTG
296 Gln Leu Gln Lys Asn Leu Thr Cys Glu Val Trp Gly Pro Thr Ser Pro Lys Leu Met Leu

AGCTTGAAACTGGAGAACAAGGAGGCAAAGGTCTCGAAGCGGGAGAAGGCGGTGTGGGTG 1080
Ser Leu Lys Leu Glu Asn Lys Glu Ala Lys Val Ser Lys Arg Glu Lys Ala Val Trp Val 335

1081 CTGAACCCTGAGGCGGGGATGTGGCAGTGTCTGCTGAGTGACTCGGGACAGGTCCTGCTG
336 Leu Asn Pro Glu Ala Gly Met Trp Gln Cys Leu Leu Ser Asp Ser Gly Gln Val Leu Leu

GAATCCAACATCAAGGTTCTGCCCACATGGTCCACCCCGGTGCAGCCAATGGCCCTGATT 1200
Glu Ser Asn Ile Lys Val Leu Pro Thr Trp Ser Thr Pro Val Gln Pro Met Ala Leu Ile 375

1201 GTGCTGGGGGGCGTCGCCGGCCTCCTGCTTTTCATTGGGCTAGGCATCTTCTTCTGTGTC
376 Val Leu Gly Gly Val Ala Gly Leu Leu Leu Phe Ile Gly Leu Gly Ile Phe Phe Cys Val

-continued

AGGTGCCGGCACCGAAGGCGCCAAGCASAGCGGATGTCTCAGATCAAGAGACTCCTCAGT 1320
Arg Cys Arg His Arg Arg Arg Gln Ala Gln Arg Met Ser Gln Ile Lys Arg Leu Leu Ser 415
Glu

1321 GAGAAGAAGACCTGCCAGTGCCCTCACCGGTTTCAGAAGACATGTAGCCCCATTTGA 1377
416 Glu Lys Lys Thr Cys Gln Cys Pro His Arg Phe Gln Lys Thr Cys Ser Pro Ile End 433 wherein

Y is C or T,

M is A or C, and

S is C or G;

or a degenerate variant thereof.

The invention also relates to a nucleic acid molecule specifying a chimpanzee CD4 fragment, comprising the following DNA sequence:

1 ATGAACCGGGGAGTCCCTTTTAGGCACTTGCTTCTGGTGCTGCAACTGGCACTCCTCCCA
−25 Met Asn Arg Gly Val Pro Phe Arg His Leu Leu Leu Val Leu Gln Leu Ala Leu Leu Pro

GCAGCCACTCAGGGAAAGAAAGTGGTGCTGGGCAAGAAAGGGGACACAGTGGAACTGACC 120
Ala Ala Thr Gln Gly Lys Lys Val Val Leu Gly Lys Lys Gly Asp Thr Val Glu Leu Thr 15

121 TGTACAGCTTCCCAGAAGAAGAGCATACAATTCCACTGGAAAAACTCCAACCAGAYAAAG
16 Cys Thr Ala Ser Gln Lys Lys Ser Ile Gln Phe His Trp Lys Asn Ser Asn Gln Thr Lys
Ile

ATTCTGGGAAATCAGGGCTCCTTCTTAACTAAAGGTCCATCCAAGCTGAATGATCGCGYT 240
Ile Leu Gly Asn Gln Gly Ser Phe Leu Thr Lys Gly Pro Ser Lys Leu Asn Asp Arg Val 55
Ala

241 GACTCAAGAAGAAGCCTTTGGGACCAAGGAAACTTTMCCCTGATCATCAAGAATCTTAAG
56 Asp Ser Arg Arg Ser Leu Trp Asp Gln Gly Asn Phe Thr Leu Ile Ile Lys Asn Leu Lys
Pro

ATAGAAGACTCAGATACTTACATCTGTGAAGTGGGGGACCAGAAGGAGGAGGTGCAATTG 360
Ile Glu Asp Ser Asp Thr Tyr Ile Cys Glu Val Gly Asp Gln Lys Glu Glu Val Gln Leu 95

361 CTAGTGTTCGGATTGACTGCCAACTCTGACACCCACCTGCTT
96 Leu Val Phe Gly Leu Thr Ala Asn Ser Asp Thr His Leu Leu wherein Y is C or T, and M is A or C;

or a degenerate variant thereof.

The invention also relates to a nucleic acid molecule specifying a gp120 binding molecule capable of glycosylation which is related to human CD4 with the cytoplasmic domain, comprising the following DNA sequence:

1 ATGAACCGGGGAGTCCCTTTTAGGCACTTGCTTCTGGTGCTGCAACTGGCACTCCTCCCA
−25 Met Asn Arg Gly Val Pro Phe Arg His Leu Leu Leu Val Leu Gln Leu Ala Leu Leu Pro

GCAGCCACTCAGGGAAAGAAAGTGGTGCTGGGCAAAAAAGGGGACACAGTGGAACTGACC 120
Ala Ala Thr Gln Gly Lys Lys Val Val Leu Gly Lys Lys Gly Asp Thr Val Glu Leu Thr 15

121 TGTACAGCTTCCCAGAAGAAGAGCATACAATTCCACTGGAAAAACTCCAACCAGAYAAAG
16 Cys Thr Ala Ser Gln Lys Lys Ser Ile Gln Phe His Trp Lys Asn Ser Asn Gln Thr Lys
Ile

ATTCTGGGAAATCAGGGCTCCTTCTTAACTAAAGGTCCATCCAAGCTGAATGATCGCGCT 240
Ile Leu Gly Asn Gln Gly Ser Phe Leu Thr Lys Gly Pro Ser Lys Leu Asn Asp Arg Ala 55

241 GACTCAAGAAGAAGCCTTTGGGACCAAGGAAACTTCMCCCTGATCATCAAGAATCTTAAG
56 Asp Ser Arg Arg Ser Leu Trp Asp Gln Gly Asn Phe Thr Leu Ile Ile Lys Asn Leu Lys
Pro

ATAGAAGACTCAGATACTTACATCTGTGAAGTGGAGGACCAGAAGGAGGAGGTGCAATTG 360
Ile Glu Asp Ser Asp Thr Tyr Ile Cys Glu Val Glu Asp Gln Lys Glu Glu Val Gln Leu 95

-continued

361 CTAGTGTTCGGATTGACTGCCAACTCTGACACCCACCTGCTTCAGGGGCAGAGCCTGACC
96 Leu Val Phe Gly Leu Thr Ala Asn Ser Asp Thr His Leu Leu Gln Gly Gln Ser Leu Thr

CTGACCTTGGAGAGCCCCCCTGGTAGTAGCCCCTCAGTGCAATGTAGGAGTCCAAGGGGT 360
Leu Thr Leu Glu Ser Pro Pro Gly Ser Ser Pro Ser Val Gln Cys Arg Ser Pro Arg Gly 135

481 AAAAACATACAGGGGGGGAAGACCCTCTCCGTGTCTCAGCTGGAGCTCCAGGATAGTGGC
136 Lys Asn Ile Gln Gly Gly Lys Thr Leu Ser Val Ser Gln Leu Glu Leu Gln Asp Ser Gly

ACCTGGACATGCACTGTCTTGCAGAACCAGAAGAAGGTGGAGTTCAAAATAGACATCGTG 600
Thr Trp Thr Cys Thr Val Leu Gln Asn Gln Lys Lys Val Glu Phe Lys Ile Asp Ile Val 175

601 GTGCTAGCTTTCCAGAAGGCCTCCAGCATAGTCTATAAGAAAGAGGGGGAACAGGTGGAG
176 Val Leu Ala Phe Gln Lys Ala Ser Ser Ile Val Tyr Lys Lys Glu Gly Glu Gln Val Glu

TTCTCCTTCCCACTCGCCTTTACAGTTGAAAAGCTGACGGGCAGTGGCGAGCTGTGGTGG 720
Phe Ser Phe Pro Leu Ala Phe Thr Val Glu Lys Leu Thr Gly Ser Gly Glu Leu Trp Trp 215

721 GACGCGGAGAGGGCTTCCTCCTCCAAGTCTTGGATCACCTTTGACCTGAAGAACAAGGAA
216 Gln Ala Glu Arg Ala Ser Ser Ser Lys Ser Trp Ile Thr Phe Asp Leu Lys Asn Lys Glu

GTGTCTGTAAAACGGGTTACCCAGGACCCTAAGCTCCAGATGGGCAAGAAGCTCCCGCTC 840
Val Ser Val Lys Arg Val Thr Gln Asp Pro Lys Leu Gln Met Gly Lys Lys Leu Pro Leu 255

841 CACCTCACCCTGCCCCAGGCCTTGCCTCAGTATGCTGGCTCTGGAAACCTCACCCTGGCC
256 His Leu Thr Leu Pro Gln Ala Leu Pro Gln Tyr Ala Gly Ser Gly Asn Leu Thr Leu Ala

CTTGAAGCGAAAACAGGAAAGTTGCATCAGGAAGTGAACCTCGTGGTGATGAGAGCCACT 840
Leu Glu Ala Lys Thr Gly Lys Leu His Gln Glu Val Asn Leu Val Val Met Arg Ala Thr 295

961 CAGCTCCAGAAAAATTTGACCTGTGAGGTGTGGGGACCCACCTCCCCTAAGCTGATGCTG
296 Gln Leu Gln Lys Asn Leu Thr Cys Glu Val Trp Gly Pro Thr Ser Pro Lys Leu Met Leu

AGCTTGAAACTGGAGAACAAGGAGGCAAAGGTCTCGAAGCGGGAGAAGGCGGTGTGGGTG 1080
Ser Leu Lys Leu Glu Asn Lys Glu Ala Lys Val Ser Lys Arg Glu Lys Ala Val Trp Val 335

1081 CTGAACCCTGAGGCGGGGATGTGGCAGTGTCTGCTGAGTGACTCGGGACAGGTCCTGCTG
336 Leu Asn Pro Glu Ala Gly Met Trp Gln Cys Leu Leu Ser Asp Ser Gly Gln Val Leu Leu

GAATCCAACATCAAGGTTCTGCCCACATGGTCCACCCCGGTGCAGCCAATGGCCCTGATT 1200
Glu Ser Asn Ile Lys Val Leu Pro Thr Trp Ser Thr Pro Val Gln Pro Met Ala Leu Ile 375

1201 GTGCTGGGGGGCGTCGCCGGCCTCCTGCTTTTCATTGGGCTAGGCATCTTCTTCTGTGTC
376 Val Leu Gly Gly Val Ala Gly Leu Leu Leu Phe Ile Gly Leu Gly Ile Phe Phe Cys Val

AGGTGCCGGCACCGAAGGCGCCAAGCAGAGCGGATGTCTCAGATCAAGAGACTCCTCAGT 1320
Arg Cys Arg His Arg Arg Arg Gln Ala Glu Arg Met Ser Gln Ile Lys Arg Leu Leu Ser 415

1321 GAGAAGAAGACCTGCCAGTGCCCTCACCGGTTTCAGAAGACATGTAGCCCCATTTGA 1377
416 Glu Lys Lys Thr Cys Gln Cys Pro His Arg Phe Gln Lys Thr Cys Ser Pro Ile End 433 wherein
Y is C or T, and
M is A or C;
or a degenerate variant thereof;

with the proviso that both Y is not T and M is not C at the same time.

The invention also relates to a nucleic acid molecule specifying a gp120 binding molecule capable of glycosylation which is related to a human CD4 fragment, comprising the following DNA sequence:

1 ATGAACCGGGGAGTCCCTTTTAGGCACTTGCTTCTGGTGCTGCAACTGGCGCTCCTCCCA
−25 Met Asn Arg Gly Val Pro Phe Arg His Leu Leu Leu Val Leu Gln Leu Ala Leu Leu Pro

-continued

```
    GCAGCCACTCAGGGAAAGAAAGTGGTGCTGGGCAAAAAAGGGGATACAGTGGAACTGACC  120
    Ala Ala Thr Gln Gly Lys Lys Val Val Leu Gly Lys Lys Gly Asp Thr Val Glu Leu Thr  15

121 TGTACAGCTTCCCAGAAGAAGAGCATACAATTCCACTGGAAAAACTCCAACCAGAYAAAG
 16 Cys Thr Ala Ser Gln Lys Lys Ser Ile Gln Phe His Trp Lys Asn Ser Asn Gln Thr Lys
                                                                        Ile

    ATTCTGGGAAATCAGGGCTCCTTCTTAACTAAAGGTCCATCCAAGCTGAATGATCGCGCT  240
    Ile Leu Gly Asn Gln Gly Ser Phe Leu Thr Lys Gly Pro Ser Lys Leu Asn Asp Arg Ala  55

241 GACTCAAGAAGAAGCCTTTGGGACCAAGGAAACTTCMCCCTGATCATCAAGAATCTTAAG
 56 Asp Ser Arg Arg Ser Leu Trp Asp Gln Gly Asn Phe Thr Leu Ile Ile Lys Asn Leu Lys
                                                Pro

    ATAGAAGACTCAGATACTTACATCTGTGAAGTGGAGGACCAGAAGGAGGAGGTGCAATTG  360
    Ile Glu Asp Ser Asp Thr Tyr Ile Cys Glu Val Glu Asp Gln Lys Glu Glu Val Gln Leu  95

361 CTAGTGTTCGGATTGACTGCCAACTCTGACACCCACCTGCTT
 96 Leu Val Phe Gly Leu Thr Ala Asn Ser Asp Thr His Leu Leu
```

wherein

Y is C or T, and

M is A or C;

or a degenerate variant thereof;

with the proviso that both Y is not T and M is not C at the same time.

The invention also relates to a nucleic acid molecule specifying a fusion protein, comprising 1) a nucleic acid molecule specifying non-human primate CD4 or fragment thereof which binds HIV or SIV gp120, and
2) a nucleic acid molecule specifying an immunoglobulin light or heavy chain, wherein the nucleic acid molecule which specifies the variable region of said immunoglobulin chain has been replaced with the nucleic acid molecule specifying said non-human primate CD4 or fragment thereof.

The invention also relates to a nucleic acid molecule specifying a fusion protein, comprising 1) a nucleic acid molecule specifying non-human primate CD4, or fragment thereof which binds HIV or SIV gp120, linked to
2) a nucleic acid molecule specifying a cytotoxic polypeptide.

The invention also relates to vectors comprising the nucleic acid molecules of the invention.

The invention also relates to hosts transformed with the vectors of the invention. In particular, the invention relates to hosts which express complementary immunoglobulin light or heavy chains together with the expression product of said fusion protein nucleic acid molecule to give an immunoglobulin-like molecule which binds to HIV or SIV gp120.

The invention also relates to methods of producing non-human primate CD4, or fragment thereof which binds to HIV or SIV gp120, which comprises cultivating in a nutrient medium under protein-producing conditions, a host strain transformed with a vector containing a nucleic acid molecule specifying a non-human primate CD4 or soluble fragment thereof which binds HIV or SIV gp120, said vector further comprising expression signals which are recognized by said host strain and direct expression of said non-human primate CD4 or fragment thereof, and recovering the non-human primate CD4 or soluble fragment thereof so produced.

The invention also relates to a method of producing a fusion protein comprising non-human primate CD4, or fragment thereof which binds to gp120, and an immunoglobulin light or heavy chain, wherein the variable region of the immunoglobulin chain has been substituted with non-human primate CD4, or fragment thereof which binds to HIV or SIV gp120, which comprises cultivating in a nutrient medium under protein-producing conditions, a host strain transformed with a vector specifying said fusion protein, said vector further comprising expression signals which are recognized by said host strain and direct expression of said fusion protein, and recovering the fusion protein so produced.

In particular, the invention relates to a method of preparing a immunoglobulin-like molecule, wherein said host strain is a myeloma cell line which produces immunoglobulin light chains and said fusion protein comprises an immunoglobulin heavy chain of the class IgM, IgG1 or IgG3, wherein an immunoglobulin-like molecule comprising said fusion protein is produced. The invention also relates to a method of preparing an immunoglobulin-like molecule, wherein said host produces immunoglobulin heavy chains of the class IgM, IgG1 and IgG3 together with said fusion protein comprising an immunoglobulin light chain to give an immunoglobulin-like molecule which binds to HIV or SIV gp120.

The invention also relates to substantially pure non-human primate CD4. In particular, the invention relates to substantially pure rhesus CD4 comprising the following amino acid sequence:

MetAsnArgGlyIleProPheArgHisLeuLeuLeuValLeuGlnLeuAlaLeuLeuPro
AlaValThrGlnGlyLysLysValValLeuGlyLysLysGlyAspThrValGluLeuThr
CysThrAlaSerGlnLysLysAsnThrGlnPheHisTrpLysAsnSerAsnGlnIleLys
IleLeuGlyIleGlnGlyLeuPheLeuThrLysGlyProSerLysLeuSerAspArgAla

-continued

AspSerArgLysSerLeuTrpAspGlnGlyCysPheSerMetIleIleLysAsnLeuLys
IleGluAspSerAspThrTyrIleCysGluValGluAsnLysLysGluGluValGluLeu
LeuValPheGlyLeuThrAlaAsnSerAspThrHisLeuLeuGluGlyGlnSerLeuThr
LeuThrLeuGluSerProProGlySerSerProSerValLysCysArgSerProGlyGly
LysAsnIleGlnGlyGlyArgThrIleSerValProGlnLeuGluArgGlnAspSerGly
ThrTrpThrCysThrValSerGlnAspGlnLysThrValGluPheLysIleAspIleVal
ValLeuAlaPheGlnLysAlaSerSerThrValTyrLysLysGluGlyGluGlnValGlu
PheSerPheProLeuAlaPheThrLeuGluLysLeuThrGlySerGlyGluLeuTrpTrp
GlnAlaGluArgAlaSerSerSerLysSerTrpIleThrPheAspLeuLysAsnLysGlu
ValSerValLysArgValThrGlnAspProLysLeuGlnMetGlyLysLysLeuProLeu
HisLeuThrLeuProGlnAlaLeuProGlnTyrAlaGlySerGlyAsnLeuThrLeuAla
LeuGluAlaLysThrGlyLysLeuHisGlnGluValAsnLeuValValMetArgAlaThr
GlnPheGlnGluAsnLeuThrCysGluValTrpGlyProThrSerProLysLeuThrLeu
SerLeuLysLeuGluAsnLysGlyAlaThrValSerLysGlnAlaLysAlaValTrpVal
LeuAsnProGluAlaGlyMetTrpGlnCysLeuLeuSerAspSerGlyGlnValLeuLeu
GluSerAsnIleLysValValProThrTrpProThrProValGlnProMetAlaLeuIle
ValLeuGlyGlyValAlaGlyLeuLeuLeuPheThrGlyLeuGlyIlePhePheCysVal
ArgCysArgHisArgArgArgGlnAlaGluArgMetSerGlnIleLysArgLeuLeuSer
GluLysLysThrCysGlnCysProHisArgPheGlnLysThrCysSerProIle.

The invention also relates to substantially pure chimpanzee CD4 comprising the following amino acid sequence:

MetAsnArgGlyValProPheArgHisLeuLeuLeuValLeuGlnLeuAlaLeuLeuPro
AlaAlaThrGlnGlyLysLysValValLeuGlyLysLysGlyAspThrValGluLeuThr
CysThrAlaSerGlnLysLysSerIleGlnPheHisTrpLysAsnSerAsnGlnThrLys
IleLeuGlyAsnGlnGlySerPheLeuThrLysGlyProSerLysLeuAsnAspArgVal
AspSerArgArgSerLeuTrpAspGlnGlyAsnPheThrLeuIleIleLysAsnLeuLys
IleGluAspSerAspThrTyrIleCysGluValGlyAspGlnLysGluGluValGlnLeu
LeuValPheGlyLeuThrAlaAsnSerAspThrHisLeuLeuGlnGlyGlnSerLeuThr
LeuThrLeuGluSerProProGlySerSerProSerValGlnCysArgSerProArgGly
LysAsnIleGlnGlyGlyLysThrLeuSerValSerGlnLeuGluLeuGlnAspSerGly
ThrTrpThrCysThrValLeuGlnAsnGlnLysLysValGluPheLysIleAspIleVal
ValLeuAlaPheGlnLysAlaSerSerIleValTyrLysLysGluGlyGluGlnValGlu
PheSerPheProLeuAlaPheThrValGluLysLeuThrGlySerGlyGluLeuTrpTrp
GlnAlaGluArgAlaSerSerSerLysSerTrpIleThrPheAspLeuLysAsnLysGlu
ValSerValLysArgValThrGlnAspProLysLeuGlnMetGlyLysLysLeuProLeu
HisLeuThrLeuProGlnAlaLeuProGlnTyrAlaGlySerGlyAsnLeuThrLeuAla
LeuGluAlaLysThrGlyLysLeuHisGlnGluValAsnLeuValValMetArgAlaThr
GlnLeuGlnLysAsnLeuThrCysGluValTrpGlyProThrSerProLysLeuMetLeu
SerLeuLysLeuGluAsnLysGluAlaLysValSerLysArgGluLysAlaValTrpVal
LeuAsnProGluAlaGlyMetTrpGlnCysLeuLeuSerAspSerGlyGlnValLeuLeu
GluSerAsnIleLysValLeuProThrTrpSerThrProValGlnProMetAlaLeuIle
ValLeuGlyGlyValAlaGlyLeuLeuLeuPheIleGlyLeuGlyIlePhePheCysVal
ArgCysArgHisArgArgArgGlnAlaGlnArgMetSerGlnIleLysArgLeuLeuSer
GluLysLysThrCysGlnCysProHisArgPheGlnLysThrCysSerProIle; or
the glycosylated derivative thereof.

The invention also relates to a substantially pure non-human CD4 molecule comprising the following amino acid sequence:

MetAsnArgGlyValProPheArgHisLeuLeuLeuValLeuGlnLeuAlaLeuLeuPro
AlaAlaThrGlnGlyLysLysValValLeuGlyLysLysGlyAspThrValGluLeuThr
CysThrAlaSerGlnLysLysSerIleGlnPheHisTrpLysAsnSerAsnGln-@-Lys
IleLeuGlyAsnGlnGlySerPheLeuThrLysGlyProSerLysLeuAsnAspArg-#-
AspSerArgArgSerLeuTrpAspGlnGlyAsnPhe-$-LeuIleIleLysAsnLeuLys
IleGluAspSerAspThrTyrIleCysGluValGlyAspGlnLysGluGluValGlnLeu
LeuValPheGlyLeuThrAlaAsnSerAspThrHisLeuLeuGlnGlyGlnSerLeuThr
LeuThrLeuGluSerProProGlySerSerProSerValGlnCysArgSerProArgGly
LysAsnIleGlnGlyGlyLysThrLeuSerValSerGlnLeuGluLeuGlnAspSerGly
ThrTrpThrCysThrValLeuGlnAsnGlnLysLysValGluPheLysIleAspIleVal
ValLeuAlaPheGlnLysAlaSerSerIleValTyrLysLysGluGlyGluGlnValGlu
PheSerPheProLeuAlaPheThrValGluLysLeuThrGlySerGlyGluLeuTrpTrp
GlnAlaGluArgAlaSerSerSerLysSerTrpIleThrPheAspLeuLysAsnLysGlu
ValSerValLysArgValThrGlnAspProLysLeuGlnMetGlyLysLysLeuProLeu
HisLeuThrLeuProGlnAlaLeuProGlnTyrAlaGlySerGlyAsnLeuThrLeuAla
LeuGluAlaLysThrGlyLysLeuHisGlnGluValAsnLeuValValMetArgAlaThr
GlnLeuGlnLysAsnLeuThrCysGluValTrpGlyProThrSerProLysLeuMetLeu
SerLeuLysLeuGluAsnLysGluAlaLysValSerLysArgGluLysAlaValTrpVal
LeuAsnProGluAlaGlyMetTrpGlnCysLeuLeuSerAspSerGlyGlnValLeuLeu
GluSerAsnIleLysValLeuProThrTrpSerThrProValGlnProMetAlaLeuIle
ValLeuGlyGlyValAlaGlyLeuLeuLeuPheIleGlyLeuGlyIlePhePheCysVal
ArgCysArgHisArgArgArgGlnAla-%-ArgMetSerGlnIleLysArgLeuLeuSer
GluLysLysThrCysGlnCysProHisArgPheGlnLysThrCysSerProIle, wherein -@- is Thr or Ile,
-#- is Val or Ala,
-$- is Thr or Pro, and
-%- is Gln or Glu; or
the glycosylated derivative thereof.

The invention also relates to a gp120 binding molecule related to human CD4, comprising the following amino acid sequence:

MetAsnArgGlyValProPheArgHisLeuLeuLeuValLeuGlnLeuAlaLeuLeuPro
AlaAlaThrGlnGlyLysLysValValLeuGlyLysLysGlyAspThrValGluLeuThr
CysThrAlaSerGlnLysLysSerIleGlnPheHisTrpLysAsnSerAsnGln-@-Lys
IleLeuGlyAsnGlnGlySerPheLeuThrLysGlyProSerLysLeuAsnAspArgAla
AspSerArgArgSerLeuTrpAspGlnGlyAsnPhe-$-LeuIleIleLysAsnLeuLys
IleGluAspSerAspThrTyrIleCysGluValGluAspGlnLysGluGluValGlnLeu
LeuValPheGlyLeuThrAlaAsnSerAspThrHisLeuLeuGlnGlyGlnSerLeuThr
LeuThrLeuGluSerProProGlySerSerProSerValGlnCysArgSerProArgGly
LysAsnIleGlnGlyGlyLysThrLeuSerValSerGlnLeuGluLeuGlnAspSerGly
ThrTrpThrCysThrValLeuGlnAsnGlnLysLysValGluPheLysIleAspIleVal
ValLeuAlaPheGlnLysAlaSerSerIleValTyrLysLysGluGlyGluGlnValGlu
PheSerPheProLeuAlaPheThrValGluLysLeuThrGlySerGlyGluLeuTrpTrp
GlnAlaGluArgAlaSerSerSerLysSerTrpIleThrPheAspLeuLysAsnLysGlu
ValSerValLysArgValThrGlnAspProLysLeuGlnMetGlyLysLysLeuProLeu
HisLeuThrLeuProGlnAlaLeuProGlnTyrAlaGlySerGlyAsnLeuThrLeuAla
LeuGluAlaLysThrGlyLysLeuHisGlnGluValAsnLeuValValMetArgAlaThr
GlnLeuGlnLysAsnLeuThrCysGluValTrpGlyProThrSerProLysLeuMetLeu
SerLeuLysLeuGluAsnLysGluAlaLysValSerLysArgGluLysAlaValTrpVal
LeuAsnProGluAlaGlyMetTrpGlnCysLeuLeuSerAspSerGlyGlnValLeuLeu
GluSerAsnIleLysValLeuProThrTrpSerThrProValGlnProMetAlaLeuIle
ValLeuGlyGlyValAlaGlyLeuLeuLeuPheIleGlyLeuGlyIlePhePheCysVal
ArgCysArgHisArgArgArgGlnAlaGluArgMetSerGlnIleLysArgLeuLeuSer
GluLysLysThrCysGlnCysProHisArgPheGlnLysThrCysSerProIle, wherein
-@- is Thr or Ile, and
-$- is Thr or Pro; or
the glycosylated derivative thereof;
with the proviso that at least one of -@- and -$- is Thr.

The invention also relates to non-human primate CD4 fragments which binds to HIV or SIV gp120. Preferably, such non-human primate CD4 fragments are soluble in aqueous solution.

In particular, the invention relates to a soluble CD4 fragment which is derived from the rhesus monkey and comprises the following amino acid sequence:

MetAsnArgGlyIleProPheArgHisLeuLeuLeuValLeuGlnLeuAlaLeuLeuPro
AlaValThrGlnGlyLysLysValValLeuGlyLysLysGlyAspThrValGluLeuThr
CysThrAlaSerGlnLysLysAsnThrGlnPheHisTrpLysAsnSerAsnGlnIleLys
IleLeuGlyIleGlnGlyLeuPheLeuThrLysGlyProSerLysLeuSerAspArgAla
AspSerArgLysSerLeuTrpAspGlnGlyCysPheSerMetIleIleLysAsnLeuLys
IleGluAspSerAspThrTyrIleCysGluValGluAsnLysLysGluGluValGluLeu
LeuValPheGlyLeuThrAlaAsnSerAspThrHisLeuLeu.

The invention also relates to a soluble chimpanzee CD4 fragment comprising the following amino acid sequence:

MetAsnArgGlyValProPheArgHisLeuLeuLeuValLeuGlnLeuAlaLeuLeuPro
AlaAlaThrGlnGlyLysLysValValLeuGlyLysLysGlyAspThrValGluLeuThr
CysThrAlaSerGlnLysLysSerIleGlnPheHisTrpLysAsnSerAsnGlnThrLys
IleLeuGlyAsnGlnGlySerPheLeuThrLysGlyProSerLysLeuAsnAspArgVal
AspSerArgArgSerLeuTrpAspGlnGlyAsnPheThrLeuIleIleLysAsnLeuLys
IleGluAspSerAspThrTyrIleCysGluValGlyAspGlnLysGluGluValGlnLeu
LeuValPheGlyLeuThrAlaAsnSerAspThrHisLeuLeu.

The invention also relates to a gp120 binding molecule capable of glycosylation comprising the following amino acid sequence:

MetAsnArgGlyValProPheArgHisLeuLeuLeuValLeuGlnLeuAlaLeuLeuPro
AlaAlaThrGlnGlyLysLysValValLeuGlyLysLysGlyAspThrValGluLeuThr
CysThrAlaSerGlnLysLysSerIleGlnPheHisTrpLysAsnSerAsnGln-@-Lys
IleLeuGlyAsnGlnGlySerPheLeuThrLysGlyProSerLysLeuAsnAspArg-#-
AspSerArgArgSerLeuTrpAspGlnGlyAsnPhe-$-LeuIleIleLysAsnLeuLys
IleGluAspSerAspThrTyrIleCysGluValGlyAspGlnLysGluGluValGlnLeu
LeuValPheGlyLeuThrAlaAsnSerAspThrHisLeuLeu wherein
-@- is Thr or Ile,
-#- is Val or Ala, and
-$- is Thr or Pro; or
the glycosylated derivative thereof.

The invention also relates to gp120 binding molecule capable of glycosylation related to human CD4 fragments. In particular, the invention relates to a glycosylated human CD4 fragment comprising the following amino acid sequence:

MetAsnArgGlyValProPheArgHisLeuLeuLeuValLeuGlnLeuAlaLeuLeuPro
AlaAlaThrGlnGlyLysLysValValLeuGlyLysLysGlyAspThrValGluLeuThr
CysThrAlaSerGlnLysLysSerIleGlnPheHisTrpLysAsnSerAsnGln-@-Lys
IleLeuGlyAsnGlnGlySerPheLeuThrLysGlyProSerLysLeuAsnAspArgAla
AspSerArgArgSerLeuTrpAspGlnGlyAsnPhe-$-LeuIleIleLysAsnLeuLys
IleGluAspSerAspThrTyrIleCysGluValGluAspGlnLysGluGluValGlnLeu
LeuValPheGlyLeuThrAlaAsnSerAspThrHisLeuLeu wherein
-@- is Thr or Ile, and -$- is Thr or Pro; or the glycosylated derivative thereof;

with the proviso that at least one of -@- and -$- is Thr.

The invention also relates to fusion proteins, comprising non-human primate CD4 or gp120 binding molecules of the invention, or HIV or SIV binding fragments thereof, linked to a cytotoxic polypeptide.

The invention also relates to a fusion protein comprising non-human primate CD4 or gp120 binding molecules of the invention, or fragments thereof which are capable of binding to HIV or SIV gp120, fused at the C-terminus to a second protein which comprises an immunoglobulin heavy chain of the class IgM, IgG1 or IgG3, wherein the variable region of said heavy chain immunoglobulin has been replaced with CD4, or HIV gp120-binding fragment thereof.

The invention also relates to an immunoglobulin-like molecule, comprising:

(1) a fusion protein of non-human primate CD4 or fragment thereof which binds to HIV or SIV gp120 and an immunoglobulin heavy chain, 1 inked to (2) an immunoglobulin light chain.

The invention also relates to a fusion protein comprising non-human primate CD4 or gp120 binding molecules of the invention, or fragment thereof which binds to HIV or SIV gp120, fused at the C-terminus to a second protein comprising an immunoglobulin light chain where the variable region has been deleted.

The invention also relates to an immunoglobulin-like molecule comprising:

1) a fusion protein of non-human primate CD4 or gp120 binding molecule of the invention, or fragment thereof which binds to HIV or SIV gp120, and an immunoglobulin light chain, linked to 2) an immunoglobulin heavy chain.

The invention also relates to pharmaceutical compositions, comprising 1) a therapeutically effective amount of a non-human primate CD4, and 2) a pharmaceutically acceptable carrier.

The invention also relates to pharmaceutical compositions, comprising 1) a therapeutically effective amount of a soluble non-human CD4 fragment, and 2) a pharmaceutically acceptable carrier.

The invention also relates to pharmaceutical compositions comprising the proteins, glycoproteins, fusion proteins and immunoglobulin-like molecules of the invention.

The invention also relates to complexes between the substantially pure non-human primate CD4 and HIV or SIV gp120.

The invention also relates to complexes comprising the non-human primate CD4 fragments of the invention and HIV or SIV gp120.

The invention also relates to complexes comprising the fusion proteins and immunoglobulin-like molecules of the invention and HIV or SIV gp120.

The invention also relates to complexes between the gp120 binding molecules capable of glycosylation and HIV or SIV gp120.

The invention also relates to a method of treating HIV or SIV infections, comprising administering to an animal in need of such treatment a therapeutically effective amount of substantially pure non-human primate CD4, or a soluble fragment thereof.

The invention also relates to a method of treating HIV or SIV infections, comprising administering to an animal in need of such treatment a therapeutically effective amount one of the fusion proteins of the invention.

The invention also relates to a method of treating HIV or SIV infections, comprising administering to an animal in need of such treatment a therapeutically effective amount one of the immunoglobulin-like molecules of the invention.

The invention also relates to a method of treating HIV or SIV infections, comprising administering to an animal in need of such treatment a therapeutically effective amount of the gp120 binding molecules of the invention.

The invention also relates to a method for the detection of HIV or SIV gp120 in a sample, comprising:

(a) contacting a sample suspected of containing HIV or SIV gp120 with the fusion protein or immunoglobulin-like molecule of the invention; and (b) detecting whether a complex is formed.

The invention also relates to a method for the detection of HIV or SIV gp120 in a sample, comprising (a) contacting a sample suspected of containing HIV or SIV gp120 with substantially pure non-human primate CD4, or fragment thereof which binds to HIV or SIV gp120, and (b) detecting whether a complex has formed.

The invention is related to the discovery that non-human primates have CD4 of differing amino acid sequence than human CD4. The invention is also related to the discovery that when non-human primate CD4 is expressed on the surface of human cells, strikingly fewer multinucleated giant cells, or syncytia, are formed than when human CD4 is expressed on the surface of the cell. The invention is also related to the discovery that the presence of a glycine residue at position 87 in the non-human primate CD4 derived from the chimpanzee, instead of the glutamic acid residue as found in human CD4, is responsible for the lack of syncytia formation.

The invention is also related to the unexpected discovery that chimpanzee CD4 contains two glycosylation sites (positions 32 and 66 (ASN)). This discovery allows for the preparation of glycosylated gp120 binding molecules and fragments thereof which bind to gp120 and likely have enhanced stability in vivo. Advantageously, the glycosylated gp120 binding molecules and fragments thereof may be administered less frequently to an animal than human or other primate CD4 molecules which are not glycosylated. Thus, the invention also relates to primate (including human) CD4 molecules having one or more glycosylation sites, for example, the chimp sequence at amino acid reidues 34 and 68, at 34 only, and at 68 only. The invention also relates to other CD4 molecules with glycosylation sites at different positions, so long as the molecule retains binding to gp120.

DESCRIPTION OF THE PREFERRED EMBODIMENTS

The invention is directed to nucleic acid molecules specifying non-human primate CD4, HIV gp120 binding fragments thereof, HIV gp120 binding soluble fragments thereof, fusion proteins thereof, and immunoglobulin-like molecules. The invention also relates to gp120 binding molecules capable of being glycosylated, HIV gp120 binding fragments thereof, fusion proteins thereof, and immunoglobulin-like molecules thereof.

The nucleic acid molecules of the invention may be a DNA or RNA molecule.

By the term "soluble" is intended that the CD4 fragment is soluble in aqueous solutions which include, but are not limited to, detergent-free aqueous buffers and body fluids such as blood, plasma and serum.

The invention is also directed to the expression of these novel nucleic acid molecules in transformed hosts to give proteins and glycoproteins.

In particular, the invention relates to expressing said nucleic acid molecules, which specify a fusion protein comprising an immunoglobulin light or heavy chain, in mammalian hosts which express complementary light or heavy chain immunoglobulins to give an immunoglobulin-like molecule which binds to HIV or SIV gp120.

By the terms "HIV infections" is intended the condition of having AIDS, AIDS related complex (ARC) or where an animal harbors the AIDS virus, but does not exhibit the clinical symptoms of AIDS or ARC. By the terms "SIV infections" is intended the condition of being infected with simian immunodeficiency virus.

By the term "animal" is intended all animals which may derive benefit from the administration of the CD4 proteins, glycoproteins, CD4 fragments, gp120 binding molecules, fusion proteins and immunoglobulin-like molecules of the invention. Foremost among such animals are humans, however, the invention is not intended to be so limited.

By the term "fusion protein" is intended a fused protein comprising a CD4 molecule of the invention, or fragment thereof which is capable of binding to gp120, linked at its C-terminus to an immunoglobulin chain wherein a portion of the N-terminus of the immunoglobulin is replaced with non-human primate CD4. Alternatively, the CD4 molecule or fragment thereof may be linked to a cytotoxic polypeptide such as ricin or diphtheria toxin.

By the term "non-human primate" is intended any member of the suborder Anthropoidea except for the family Hominidae. Such non-human primates include the superfamily Ceboidea, family Cebidae (the New World monkeys including the capuchins, howlers, spider monkeys and squirrel monkeys) and family Callithricidae (including the marmosets); the superfamily Cercopithecoidea, family Cercopithecidae (including the macaques, mandrills, baboons, proboscis monkeys, mona monkeys, and the sacred hanuman monkeys of India); and superfamily Hominoidae, family Pongidae (including gibbons, orangutans, gorillas, and chimpanzees). The rhesus monkey is one member of the macaques.

The nucleic acid molecules and proteins of the invention may be prepared according to the methods disclosed herein and according to well known methods of solid phase synthesis using the amino acid and DNA sequences disclosed herein.

As described more fully in the examples below, the gly residue at position 87 of the CD4 derived from the chimpanzee differs from the Glu residue present in human CD4 which is responsible for syncytium formation. This discovery allows for the preparation of new CD4 molecules which do not mediate syncytium formation. An example of such a protein related to the chimpanzee CD4 molecule comprises the following amino acid sequence:

MetAsnArgGlyValProPheArgHisLeuLeuLeuValLeuGlnLeuAlaLeuLeuPro
AlaAlaThrGlnGlyLysLysValValLeuGlyLysLysGlyAspThrValGluLeuThr
CysThrAlaSerGlnLysLysSerIleGlnPheHisTrpLysAsnSerAsnGln-@-Lys
IleLeuGlyAsnGlnGlySerPheLeuThrLysGlyProSerLysLeuAsnAspArg-#-
AspSerArgArgSerLeuTrpAspGlnGlyAsnPhe-$-LeuIleIleLysAsnLeuLys
IleGluAspSerAspThrTyrIleCysGluValGlyAspGlnLysGluGluValGlnLeu
LeuValPheGlyLeuThrAlaAsnSerAspThrHisLeuLeuGlnGlyGlnSerLeuThr
LeuThrLeuGluSerProProGlySerSerProSerValGlnCysArgSerProArgGly
LysAsnIleGlnGlyGlyLysThrLeuSerValSerGlnLeuGluLeuGlnAspSerGly
ThrTrpThrCysThrValLeuGlnAsnGlnLysLysValGluPheLysIleAspIleVal
ValLeuAlaPheGlnLysAlaSerSerIleValTyrLysLysGluGlyGluGlnValGlu
PheSerPheProLeuAlaPheThrValGluLysLeuThrGlySerGlyGluLeuTrpTrp
GlnAlaGluArgAlaSerSerSerLysSerTrpIleThrPheAspLeuLysAsnLysGlu
ValSerValLysArgValThrGlnAspProLysLeuGlnMetGlyLysLysLeuProLeu
HisLeuThrLeuProGlnAlaLeuProGlnTyrAlaGlySerGlyAsnLeuThrLeuAla
LeuGluAlaLysThrGlyLysLeuHisGlnGluValAsnLeuValValMetArgAlaThr
GlnLeuGlnLysAsnLeuThrCysGluValTrpGlyProThrSerProLysLeuMetLeu
SerLeuLysLeuGluAsnLysGluAlaLysValSerLysArgGluLysAlaValTrpVal
LeuAsnProGluAlaGlyMetTrpGlnCysLeuLeuSerAspSerGlyGlnValLeuLeu
GluSerAsnIleLysValLeuProThrTrpSerThrProValGlnProMetAlaLeuIle
ValLeuGlyGlyValAlaGlyLeuLeuLeuPheIleGlyLeuGlyIlePhePheCysVal
ArgCysArgHisArgArgArgGlnAla-%-ArgMetSerGlnIleLysArgLeuLeuSer
GluLysLysThrCysGlnCysProHisArgPheGlnLysThrCysSerProIle, wherein -@- is Thr or Ile,
-#- is Val or Ala,
-$- is Thr or Pro, and
-%- is Gln or Glu, or the glycosylated derivative thereof.

The recombinant DNA molecules which encode this family of proteins and glycoproteins have the following sequence:

```
  1 ATGAACCGGGGAGTCCCTTTTAGGCACTTGCTTCTGGTGCTGCAACTGGCACTCCTCCCA
    GCAGCCACTCAGGGAAAGAAAGTGGTGCTGGGCAAGAAAGGGGACACAGTGGAACTGACC
121 TGTACAGCTTCCCAGAAGAAGAGCATACAATTCCACTGGAAAAACTCCAACCAGAYAAAG
    ATTCTGGGAAATCAGGGCTCCTTCTTAACTAAAGGTCCATCCAAGCTGAATGATCGCGYT
241 GACTCAAGAAGAAGCCTTTGGGACCAAGGAAACTTTWCCCTGATCATCAAGAATCTTAAG
    ATAGAAGACTCAGATACTTACATCTGTGAAGTGGGGGACCAGAAGGAGGAGGTGCAATTG
361 CTAGTGTTCGGATTGACTGCCAACTCTGACACCCACCTGCTTCAGGGGCAGAGCCTGACC
    CTGACCTTGGAGAGCCCCCCTGGTAGTAGCCCCTCAGTGTCAATGTAGGAGTCCAAGGGGT
```

-continued

```
481 AAAAACATACAGGGGGGGAAGACCCTCTCCGTGTCTCAGCTGGAGCTCCAGGATAGTGGC
    ACCTGGACATGCACTGTCTTGCAGAACCAGAAGAAAGTGGAGTTCAAAATAGACATCGTG
601 GTGCTAGCTTTCCAGAAGGCCTCCAGCATAGTCTATAAGAAAGAGGGGGAACAGGTGGAG
    TTCTCCTTCCCACTCGCCTTTACAGTTGAAAAGCTGACGGGCAGTGGCGAGCTGTGGTGG
721 CAGGCGGAGAGGGCTTCCTCCTCCAAGTCTTGGATCACCTTTGACCTGAAGAACAAGGAA
    GTGTCTGTAAAACGGGTTACCCAGGACCCTAAGCTCCAGATGGGCAAGAAGCTCCCGCTC
841 CACCTCACCCTGCCCCAGGCCTTGCCTCAGTATGCTGGCTCTGGAAACCTCACCCTGGCC
    CTTGAAGCGAAAACAGGAAAGTTGCATCAGGAAGTGAACCTCGTGGTGATGAGAGCCACT
961 CAGCTCCAGAAAAATTTGACCTGTGAGGTGTGGGGACCCACCTCCCCTAAGCTGATGCTG
    AGCTTGAAACTGGAGAACAAGGAGGCAAAGGTCTCGAAGCGGGAGAAGGCGGTGTGGGTG
1081 CTGAACCCTGAGGCGGGGATGTGGCAGTGTCTGCTGAGTGACTCGGGACAGGTCCTGCTG
    GAATCCAACATCAAGGTTCTGCCCACATGGTCCACCCCGGTGCAGCCAATGGCCCTGATT
1201 GTGCTGGGGGGCGTCGCCGGCCTCCTGCTTTTCATTGGGCTAGGCATCTTCTTCTGTGTC
    AGGTGCCGGCACCGAAGGCGCCAAGCASAGCGGATGTCTCAGATCAAGAGACTCCTCAGT
1321 GAGAAGAAGACCTGCCAGTGCCCTCACCGGTTTCAGAAGACATGTAGCCCCATTTGA
```

wherein

Y is C or T,

W is A or C, and

S is C or G;

or a degenerate variant thereof.

In general, for the preparation of fusion proteins comprising an immunoglobulin, that portion of immunoglobulin which is deleted is the variable region. The fusion proteins of the invention may also comprise immunoglobulins where more than just the variable region has been deleted and replaced with the CD4 molecule or HIV gp120 binding fragment thereof. For example, the $V_H$ and CH1 regions of an immunoglobulin chain may be deleted. In practice, any amount of the N-terminus of the immunoglobulin heavy chain can be deleted as long as the remaining fragment mediates cell death by antibody effector function or other mechanism. The minimum sequence required for binding complement encompasses domains CH2 and CH3. Joining of Fc portions by the hinge region is advantageous for increasing the efficiency of complement binding.

The CD4 molecules of the invention and fusion proteins thereof may comprise the complete CD4 sequence, the 372 amino acid extracellular region and the membrane spanning domain, or just the extracellular region. Moreover, the fusion proteins may comprise fragments of the extracellular region which retains binding to HIV gp120. The extracellular domain of CD4 consists of four contiguous regions each having amino acid and structural similarity to the variable and joining (V-J) domains of immunoglobulin light chains as well as related regions in other members of the immunoglobulin gene superfamily. These structurally similar regions of CD4 are termed the $V_1$, $V_2$, $V_3$ and $V_4$ domains. See PCT Application Publication Number WO 89/02922 (published Oct. 3, 1988). Thus, the non-human primate CD4 and fusion proteins thereof may comprise any combination of such binding regions. In general, any fragment of the CD4 proteins and glycoproteins of the invention may be used as long as they retain binding to gp120.

Gp120 binding CD4 fragments may be obtained by cutting the DNA sequence which encodes chimpanzee CD4 at the Nhe site at position 603 (to give a molecule which encodes two binding domains) or the BspM1 site at position 405 (to give a molecule which encodes one domain). Alternatively, the DNA molecule encoding rhesus CD4 may be cut at the Nhe site at position 603 (to give a molecule which encodes two domains) or the BspM1 site at position 405 (to give a molecule which encodes one domain). Other fragments may be obtained using, for example, an exonuclease. The DNA fragment can then be incorporated into a cloning vector and introduced into a host, followed by screening the transformed host for the presence of a protein which binds gp120. Methods for screening clones for specific binding activity are well known to those of ordinary skill in the art. Preferably, such CD4 fragments are soluble in aqueous solution.

Where the fusion protein comprises an immunoglobulin light chain, it is necessary that no more of the Ig chain be deleted than is necessary to form a stable complex with a heavy chain Ig. In particular, the cysteine residues necessary for disulfide bond formation must be preserved on both the heavy and light chain moieties.

When expressed in a host, e.g., a mammalian cell, the fusion protein may associate with other light or heavy Ig chains secreted by the cell to give a functioning immunoglobulin-like molecule which is capable of binding to gp120. The gp120 may be in solution, expressed on the surface of infected cells, or may be present on the surface of the HIV virus itself. Alternatively, the fusion protein may be expressed in a mammalian cell which does not secrete other light or heavy Ig chains. When expressed under these conditions, the fusion protein may form a homodimer.

Genomic or cDNA sequences may be used in the practice of the invention. Genomic sequences are expressed efficiently in myeloma cells, since they contain native promoter structures.

The constant regions of the antibody cloned and used in the chimeric immunoglobulin-like molecule may be derived from any mammalian source. They may be complement binding or ADCC active. The constant regions may be derived from any appropriate isotype, including IgG1, IgG3, or IgM.

The joining of various DNA fragments, is performed in accordance with conventional techniques, employing blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. The genetic construct may optionally encode a leader sequence to allow efficient expression of the fusion protein. For example, the leader sequence utilized by Maddon et al., *Cell* 42:93–104 (1985) for the expression of human CD4 may be used.

For cDNA isolation, cDNA libraries may be screened, for example, by use of a complementary probe or by assay for the expressed CD4 molecule of the invention using a CD4-specific antibody. Methods for preparing antibodies by immunizing animals with an antigen are taught, for example, by Kohler and Milstein, *Nature* (London) 256:495 (1975); Kohler et al., *Eur. J. Immunol.* 6:511 (1976); Kohler et al., *Eur. J. Immunol.* 6:292 (1976); or Hammerling et al., in: *Monoclonal Anti-*

*bodies and T-Cell Hybridomas*, Elsevier, N.Y., pp.563–681 (1981). The invention further relates to monoclonal and polyclonal antibodies which are specific for the non-human CD4 proteins, glycoproteins of the invention, and the soluble and non-soluble fragments thereof.

The non-human primate CD4 may be derived from any member of the suborder Anthropoidea except for the family Hominidae. Preferably, the non-human primate CD4 is derived from the rhesus monkey or chimpanzee, although the invention is not intended to be so limited. One of ordinary skill in the art can obtain the CD4 from any additional primate by isolation of the poly-A containing RNA of mitogen stimulated peripheral blood mononuclear cells obtained from the particular animal. After preparation of cDNA with, for example, reverse transcriptase, the cDNA may be ligated into an appropriate cloning vector and used to transform an appropriate host. The clones may then be screened with a monoclonal antibody directed to the rhesus monkey or chimpanzee CD4 of the invention followed by selection of positive clones, or by hybridization with the chimp or rhesus CD4 cDNAs.

To express the CD4 molecules and fusion hybrid proteins of the invention, transcriptional and translational signals recognized by an appropriate host element are necessary. Eukaryotic hosts which may be used include mammalian cells capable of culture in vitro, particularly leukocytes, more particularly myeloma cells or other transformed or oncogenic lymphocytes, e.g., EBV-transformed cells. Advantageously, mammalian cells are used to express the glycosylated CD4 proteins. Alternatively, non-mammalian cells may be employed, such as bacteria, fungi, e.g., yeast, filamentous fungi, or the like.

Preferred hosts for fusion protein production are mammalian cells, grown in vitro in tissue culture or in vivo in animals. Mammalian cells provide post translational modification to immunoglobulin protein molecules which provide for correct folding and glycosylation of appropriate sites. Mammalian cells which may be useful as hosts include cells of fibroblast origins such as VERO or CHO-K1 or cells of lymphoid origin, such as the hybridoma SP2/0-AG14 or the myeloma P3x63Sgh, and their derivatives. For the purpose of preparing an immunoglobulin-like molecule, a plasmid containing a gene which encodes a heavy chain immunoglobulin, wherein the variable region has been replaced with one of the CD4 molecules of the invention, may be introduced, for example, into J558L myeloma cells, a mouse plasmacytoma expressing the lambda-1 light chain but which does not express a heavy chain (see Oi et al., *P.N.A.S.* (USA) 80:825–829 (1983)). Other preferred hosts include COS cells, BHK cells and hepatoma cells.

The constructs may be joined together to form a single DNA segment or may be maintained as separate segments, by themselves or in conjunction with vectors.

Where the protein is not glycosylated, any host may be used to express the protein which is compatible with replication and transcription of sequences in the expression plasmid. In general, vectors containing replication and transcription controlling sequences are derived from species compatible with a host cell are used in connection with the host. The vector ordinarily carries a replication origin, as well as specific genes which are capable of providing phenotypic selection in transformed cells. The expression of the non-human primate CD4 molecules and fusion proteins can also be placed under control with other regulatory sequences which may be homologous to the organism in its untransformed state. For example, lactose-dependent *E. coli* chromosomal DNA comprises a lactose or lac operon which mediates lactose utilization by elaborating the enzyme betagalactosidase. The lac control elements may be obtained from bacterial phage lambda plac5, which is infective for *E. coli.* The lac promoter-operator system can be induced by IPTG.

Other promoters/operator systems or portions thereof can be employed as well. For example, colicin E1 , galactose, alkaline phosphatase, tryptophan, xylose, tax, and the like can be used.

For mammalian hosts, several possible vector systems are available for expression. One class of vectors utilize DNA elements which are derived from animal viruses such as bovine papilloma virus, polyoma virus, adenovirus, vaccinia virus, baculovirus, retroviruses (RSV, MMTV or MOMLV), or SV40 virus. Cells which have stably integrated the DNA into their chromosomes may be selected by introducing one or more markers which allow selection of transfected host cells. The marker may provide for prototropy to an auxotrophic host, biocide resistance, e.g., antibiotics, or heavy metals such as copper or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals. The cDNA expression vectors incorporating such elements includes those described by Okayama, H., *Mol. Cel. Biol.*, 3:280 (1983) and others.

Once the vector or DNA sequence containing the constructs has been prepared for expression, the DNA constructs may be introduced to an appropriate host. Various techniques may be employed, such as protoplast fusion, calcium phosphate precipitation, electroporation or other conventional techniques. After the fusion, the cells are grown in media and screened for the appropriate activity. Expression of the gene(s) results in production of the desired protein. If the expressed product is a fusion protein, it may then be subject to further assembly with an immunoglobulin light or heavy chain to form an immunoglobulin-like molecule.

The host cells for CD4 protein and glycoprotein, CD4 fragment, and immunoglobulin production may be immortalized cells, primarily myeloma or lymphoma cells. These cells may be grown in appropriate nutrient medium in culture flasks or injected into a synergistic host, e.g., mouse or a rat, or immunodeficient host or host site, e.g., nude mouse or hamster pouch. In particular, the cells may be introduced into the abdominal cavity of an animal to allow production of ascites fluid which contains the immunoglobulin-like molecule. Alternatively, the cells may be injected subcutaneously and the chimeric antibody is harvested from the blood of the host. The cells may be used in the same manner as hybridoma cells. See Diamond et al., *N. Eng. J. Med.* 304:1344 (1981), and Kennatt, McKearn and Bechtol (Eds.), *Monoclonal Antibodies: Hybridomas:—A New Dimension in Biologic Analysis*, Plenum, 1980.

The CD4 proteins, glycoproteins, CD4 fragments, fusion proteins and immunoglobulin-like molecules of the invention may be isolated and purified in accordance with conventional conditions, such as extraction, precipitation, chromatography, affinity chromatography, electrophoresis or the like. For example, the CD4 proteins, glycoproteins and fragments may be purified by passing a solution thereof through a column having gp120 immobilized thereon (see U.S. Pat. No. 4,725,669). The bound CD4 molecule may then be eluted by treatment with a chaotropic salt or by elution with aqueous acetic acid (1M) .

The Ig fusion proteins may be purified by passing a solution containing the fusion protein through a column which contains immobilized protein A or protein G which selectively binds the Fc portion of the fusion protein. See, for example, Reis, K. J., et al., *J. Immunol.* 132:3098–3102 (1984); PCT Application, Publication No. W087/00329. The chimeric antibody may the be eluted by treatment with a chaotropic salt or by elution with aqueous acetic acid (1M).

Alternatively the non-human primate CD4 proteins and glycoproteins, fragments, fusion proteins and immunoglobulin-like molecules may be purified on anti-CD4 antibody columns, or on anti-immunoglobulin antibody columns to give a substantially pure protein.

By the term "substantially pure" is intended that the protein is free of the impurities that are naturally associated therewith. Substantial purity may be evidenced by a single band by electrophoresis.

In one embodiment of the invention, cDNA sequences which encode the CD4 molecules of the invention, or a fragment thereof which binds gp120, may be ligated into an expression plasmid which codes for an antibody wherein the variable region of the gene has been deleted. Methods for the preparation of genes which encode the heavy or light chain constant regions of immunoglobulins are taught, for example, by Robinson, R. et al., PCT Application, Publication No. WO87–02671. The cDNA sequence encoding the CD4 molecule or fragment may be directly joined to the cDNA encoding the light or heavy Ig contant regions or may be joined via a linker sequence. Preferably, the linker sequence does not encode a protein product which gives rise to an antigenic reaction in the individual.

Preferred immunoglobulin-like molecules which contain the CD4 molecules of the invention, or fragments thereof, contain the constant region of an IgM, IgG1 or IgG3 antibody.

The fusion protein and immunoglobulin-like molecule may complex to gp120 which is expressed on infected cells. Although the inventor is not bound by a particular theory, it appears that the Fc portion of the fusion protein or immunoglobulin-like molecule may bind with complement to mediate destruction of the cell.

Examples of radioisotopes which can be bound to the proteins, glycoproteins, fusion proteins, and immunoglobulin-like molecules of the invention for use in HIV-therapy are $^{125}I$, $^{131}I$, $^{90}Y$, $^{67}Cu$, $^{217}Bi$, $^{211}At$, $^{212}Pb$, $^{47}Sc$, and $^{109}Pd$. Optionally, a label such as boron can be used which emits $\alpha$ and $\beta$ particles upon bombardment with neutron radiation.

For in vivo diagnosis radionucleotides may be bound to the CD4 proteins, glycoproteins or fragments thereof, fusion proteins or immunoglobulin-like molecules either directly or by using an intermediary functional group. An intermediary group which is often used to bind radioisotopes, which exist as metallic cations, to antibodies is diethylenetriaminepentaacetic acid (DTPA). Typical examples of metallic cations which are bound in this manner are $^{99m}Tc$ $^{123}I$, $^{111}In$, $^{131}I$, $^{97}Ru$, $^{67}Cu$, $^{67}Ga$, and $^{68}Ga$.

Moreover, the CD4 proteins and glycoproteins or fragments thereof, fusion proteins and immunoglobulin-like molecules may be tagged with an NMR imaging agent which include paramagnetic atoms. The use of an NMR imaging agent allows the in vivo diagnosis of the presence of and the extent of HIV infection within a patient using NMR techniques. Elements which are particularly useful in this manner are $^{157}Gd$, $^{55}Mn$, $^{162}Dy$, $^{52}Cr$, and $^{56}Fe$.

The detection and quantitation of antigenic substances and biological samples frequently utilizes immunoassay techniques. These techniques are based upon the formation of the complex between the antigenic substance, e.g., gp120, being assayed and an antibody or antibodies in which one or the other member of the complex may be detectably labeled. In the present invention, the CD4 proteins, glycoproteins or fragments thereof, immunoglobulin-like molecules or fusion proteins may be labeled with any conventional label.

Thus, the CD4 protein, glycoprotein or fragment thereof, fusion protein or immunoglobulin-like molecule can also be used in assay for HIV or SIV viral infection in a biological sample by contacting a sample, derived from an animal suspected of having an HIV or SIV infection, with the CD4 protein, glycoprotein or fragment thereof, fusion protein or immunoglobulin-like molecule, and detecting whether a complex with gp120, either alone or on the surface of an HIV-infected cell, has formed.

For example, a biological sample may be treated with nitro-cellulose, or other solid support which is capable of immobilizing cells, cell particles or soluble protein. The support may then be washed with suitable buffers followed by treatment with the CD4 protein, glycoprotein or fragment thereof, fusion protein, or immunoglobulin-like molecule, any of which may be detectably labeled. The solid phase support may then be washed with a buffer a second time to remove unbound protein and the label detected.

In carrying out the assay of the present invention on a sample containing gp120, the process comprises:

a) contacting a sample suspected of containing gp120 with a solid support to effect immobilization of gp120, or cell which expresses gp120 on its surface;
b) contacting said solid support with the detectably labeled CD4 protein, glycoprotein or fragment thereof which binds to HIV gp120, immunoglobulin-like molecule or fusion protein molecule of the invention;
c) incubating said detectably labeled molecule with said support for a sufficient amount of time to allow the detectably labelled molecule to bind to the immobilized gp120 or cell which expresses gp120 on its surface;
d) separating the solid phase support from the incubation mixture obtained in step c); and
e) detecting the bound detectably labeled molecule and thereby detecting and quantifying gp120.

Alternatively, the detectably labeled CD4 protein, glycoprotein or fragment thereof, immunoglobulin-like molecule or fusion protein-gp120 complex in a sample may be separated from a reaction mixture by contacting the complex with an immobilized antibody or protein which is specific for an immunoglobulin or, e.g., protein A, protein G, anti-IgM or anti-IgG antibodies. Such anti-immunoglobulin antibodies may be monoclonal or polyclonal. The solid support may then be washed with suitable buffers to give an immobilized complex. The label may then be detected to give a measure of gp120 and, thereby, the presence of HIV.

This aspect of the invention relates to a method for detecting HIV or SIV viral infection in a sample comprising:

(a) contacting a sample suspected of containing gp120 with a fusion protein comprising non-human primate CD4 or fragment thereof that binds to HIV gp120 and the Fc portion of an immunoglobulin chain, and (b) detecting whether a complex is formed.

The invention also relates to a method of detecting gp120 in a sample, further comprising:

(c) contacting the mixture obtained in step (a) with an Fc binding molecule, such as an antibody, protein A, or protein G, which is immobilized on a solid phase support and is specific for the fusion protein, to give a gp120 fusion protein-immobilized antibody complex (d) washing the solid phase support obtained in step (c) to remove unbound fusion protein, and (e) and detecting the label on the fusion protein.

Of course, the specific concentrations of detectably labeled immunoglobulin-like molecule (or fusion protein) and gp120, the temperature and time of incubation, as well as other assay conditions may be varied, depending on various factors including the concentration of gp120 in the sample, the nature of the sample, and the like. Those skilled in the art will be able to determine operative and optimal assay conditions for each determination by employing routine experimentation.

Other such steps as washing, stirring, shaking, filtering and the like may be added to the assays as is necessary for the particular situation.

One of the ways in which the CD4 protein, glycoprotein or fragment thereof, immunoglobulin-like molecule or fusion protein can be detectably labeled is by linking the same to an enzyme. This enzyme, in turn, when later exposed to its substrate, will catalize the formation of a product which can be detected as, for example, by spectrophotometric, fluorometric or by visual means. Enzymes which can be used to detectably label the CD4 protein, glycoprotein or fragment thereof, immunoglobulin-like molecule or fusion protein of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The CD4 protein, glycoprotein or fragment thereof, immunoglobulin-like molecule or fusion protein of the present invention may also be labeled with a radioactive isotope which can be determined by such means as the use of a gamma counter or a scintillation counter or by autoradiography. Isotopes which are particularly useful for the purpose of the present invention are: $^{3}H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$ and $^{75}Se$.

It is also possible to label the CD4 protein, glycoprotein or fragment thereof, immunoglobulin-like molecule or fusion protein with a fluorescent compound. When the fluorescently labeled immunoglobulin-like molecule is exposed to light of the proper wave length, its presence can then be detected due to the fluorescence of the dye. Among the most commonly used fluorescent labelling compounds are fluorescein isothiocyanate, rhodamine, phycoerythrin, phycocyanin, allophycocyanin, o-phthaldehyde and fluorescamine.

The CD4 protein, glycoprotein or fragment thereof, immunoglobulin-like molecule or fusion protein of the invention can also be detectably labeled using fluorescence emitting metals such as $^{152}Eu$, or others of the lanthanide series. These metals can be attached to the CD4 protein, glycoprotein or fragment thereof, immunoglobulin-like molecule or fusion protein, using such metal chelating groups as diethylenetriaminepentaacetic acid (DTPA) or ethylenediaminetetraacetic acid (EDTA).

The CD4 protein, glycoprotein or fragment thereof, immunoglobulin-like molecule or fusion protein of the present invention also can be detectably labeled by coupling it to a chemiluminescent compound. The presence of the chemiluminescent-tagged CD4 protein, glycoprotein or fragment thereof, immunoglobulin-like molecule or fusion protein is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the CD4 protein, glycoprotein or fragment thereof, immunoglobulin-like molecule or fusion protein of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the CD4 protein, glycoprotein or fragment thereof, immunoglobulin-like molecule or fusion protein may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

The assay of the present invention is ideally suited for the preparation of a kit. Such a kit may comprise a carrier means being compartmentalized to receive in close confinement therewith one or more container means such as vials, tubes and the like, each of said container means comprising the separate elements of the immunoassay. For example, there may be a container means containing a solid phase support, and further container means containing the detectably labeled CD4 protein, glycoprotein or fragment thereof, immunoglobulin-like molecule or fusion protein. Further container means may contain standard solutions comprising serial dilutions of analytes such as gp120 or fragments thereof to be detected. The standard solutions of these analytes may be used to prepare a standard curve with the concentration of gp120 plotted on the abscissa and the detection signal on the ordinate. The results obtained from a sample containing gp120 may be interpolated from such a plot to give the concentration of gp120.

The CD4 protein, glycoprotein or fragment thereof, immunoglobulin-like molecule or fusion protein of the present invention can also be used as a stain for tissue sections. For example, a labeled molecule comprising CD4 protein or glycoprotein or HIV gp120 binding fragment thereof, may be contacted with a tissue section, e.g., a brain biopsy specimen. This section may then be washed and the label detected.

The following examples are illustrative, but not limiting the method and composition of the present invention, Other suitable modifications and adaptations which are obvious to those skilled in the art are within the spirit and scope of this invention.

EXAMPLES

Example 1

Isolation of Chimpanzee and Rhesus Monkey CD4 cDNAs cDNA clones encoding the CD4 antigens of the Chimpanzee (*Pan troglodytes*) and the Rhesus Monkey (*Maccaca mulatta*) were isolated, sequenced, and expressed. Non-human primate CD4 cDNAs were synthesized from the poly-A containing RNA of mitogen stimulated peripheral blood mononuclear cells obtained from these animals. cDNA expression libraries were made in the vector CDM8 and CD4 cDNAs we isolated by four rounds of immunoselection as previously described by Seed et al., *Proc. Natl. Acad. Sci* (USA) 8-4:3365-3369 (1987). Sequencing was carried out using the dideoxynucleotide chain termination technique on single and double stranded templates. The DNA and amino acid sequences of the Chimpanzee and Rhesus Monkey CD4 are shown below. Also shown is a comparison of the respective sequences to human CD4.

Rhesus CD4 Coding Sequence and Predicted Amino Acid Sequence Showing Differences from Human Sequences

```
  1 ATGAACCGGGGAATCCCTTTTAGGCACTTGCTTCTGGTGCTGCAACTGGCGCTACTCCCA
-25 Met Asn Arg Gly Ile Pro Phe Arg His Leu Leu Leu Val Leu Gln Leu Ala Leu Leu Pro
                    Val
                    G                                                     C

                              1
                              |
    GCAGTCACCCAGGGAAAGAAAGTGGTGCTGGGCAAGAAAGGGGATACAGTGGAACTGACC     120
    Ala Val Thr Gln Gly Lys Lys Val Val Leu Gly Lys Lys Gly Asp Thr Val Glu Leu Thr 15
        Ala
         C   T                                    A

     *
121 TGTACAGCTTCGCAGAAGAAGAACACACAATTCCACTGGAAAAACTCCAACCAGATAAAG
 16 Cys Thr Ala Ser Gln Lys Lys Asn Thr Gln Phe His Trp Lys Asn Ser Asn Gln Ile Lys
                                Ser Ile

                  C              G   T

    ATTCTGGGAATTCAGGGTCTCTTCTTAACTAAAGGTCCATCCAAGCTGAGCGATCGTGCT     240
    Ile Leu Gly Ile Gln Gly Leu Phe Leu Thr Lys Gly Pro Ser Lys Leu Ser Asp Arg Ala 55
                Asn         Ser                                 Asn
                 A          CTC                                  AT        C

241 GACTCAAGAAAAAGCCTTTGGGACCAAGGATGCTTTTCCATGATCATCAAGAATCTTAAG
 56 Asp Ser Arg Lys Ser Leu Trp Asp Gln Gly Cys Phe Ser Met Ile Ile Lys Asn Leu Lys
                Arg                         Asn     Pro Leu

                 G                          AA     CC  C

                                     *
    ATAGAAGACTCAGATACTTACATCTGTGAAGTGGAGAACAAGAAGGAGGAGGTGGAATTG     360
    Ile Glu Asp Ser Asp Thr Tyr Ile Cys Glu Val Glu Asn Lys Lys Glu Glu Val Glu Leu 95
                                                Asp Gln                 Gln
                                                G   C                   C

361 CTGGTGTTCGGATTGACTGCCAACTCTGACACCCACCTGCTTGAGGGGCAAAGCCTGACC
 96 Leu Val Phe Gly Leu Thr Ala Asn Ser Asp Thr His Leu Leu Glu Gly Gln Ser Leu Thr
                                                        Gln

      A                                                 C          G

    CTGACCTTGGAGAGCCCCCCTGGTAGTAGCCCCTCAGTGAAATGTAGGAGTCCAGGGGGT     480
    Leu Thr Leu Glu Ser Pro Pro Gly Ser Ser Pro Ser Val Lys Cys Arg Ser Pro Gly Gly 135
                                                    Gln                 Arg
                                                    C                   G
```

-continued

```
 481 AAAAACATACAGGGGGGGAGGACCATCTCTGTGCCTCAGCTGGAGCGCCAGGATAGTGGC
 136 Lys Asn Ile Gln Gly Gly Arg Thr Ile Ser Val Pro Gln Leu Glu Arg Gln Asp Ser Gly
                             Lys     Leu         Ser             Leu

                              A       C       C   T                   T

     ACCTGGACATGCACCGTCTCGCAGGACCAGAAGACGGTGGAGTTCAAAATAGACATCGTG 600
     Thr Trp Thr Cys Thr Val Ser Gln Asp Gln Lys Thr Val Glu Phe Lys Ile Asp Ile Val 175
                             Leu     Asn         Lys
                         T   T       A           A

 601 GTGCTAGCTTTCCAGAAGGCCTCCAGCACAGTCTATAAGAAAGAGGGGGAACAGGTGGAG
 176 Val Leu Ala Phe Gln Lys Ala Ser Ser Thr Val Tyr Lys Lys Glu Gly Glu Gln Val Glu
                                         Ile

                                         T

     TTCTCCTTCCCACTCGCCTTTACACTTGAAAAGCTGACGGGCAGTGGCGAGCTGTGGTGG 720
     Phe Ser Phe Pro Leu Ala Phe Thr Leu Glu Lys Leu Thr Gly Ser Gly Glu Leu Trp Trp 215
                                     Val
                                     G

 721 CAGGCGGAGAGGGCCTCCTCCTCCAAGTCTTGGATTACCTTCGACCTGAAGAACAAGGAA
 216 Gln Ala Glu Arg Ala Ser Ser Ser Lys Ser Trp Ile Thr Phe Asp Leu Lys Asn Lys Glu

                          T                                  C     T

     GTGTCTGTAAAACGGGTTACCCAGGACCCCAAGCTCCAGATGGGCAAGAAGCTCCCGCTC 840
     Val Ser Val Lys Arg Val Thr Gln Asp Pro Lys Leu Gln Met Gy Lys Lys Leu Pro Leu 255
                                         T

                                                                - - - - - - - - -
 841 CACCTCACCCTGCCCCAGGCCTTGCCTCAGTATGCTGGCTCTGGAAACCTCACGCTGGCC
 256 His Leu Thr Leu Pro Gln Ala Leu Pro Gln Tyr AlA Gly Ser Gly Asn Leu Thr Leu Ala

     CTTGAAGCGAAAACAGGAAAGTTGCATCAGGAAGTGAACCTCGTGGTGATGAGAGCCACT 960
     Leu Glu Ala Lys Thr Gly Lys Leu His Gln Glu Val Asn Leu Val Val Met Arg Ala Thr 295

                                                           G

                       - - - - - - - - - *
 961 CAGTTCCAGGAAAATTTGACCTGTGAAGTGTGGGGACCCACCTCCCCTAAGCTGACGCTG
 296 Gln Phe Gln Glu Asn Leu Thr Cys Glu Val Trp Gly Pro Thr Ser Pro Lys Leu Thr Leu
         Leu     Lys                                                     Met

         C       A                   G                                   T

     AGCTTGAAACTGGAGAACAAGGGGGCAACGGTCTCGAAGCAGGCGAAGGCGGTGTGGGTG 1080
     Ser Leu Lys Leu Glu Asn Lys Gly Ala Thr Val Ser Lys Gln Ala Lys Ala Val Trp Val 335
                                 Glu     Lys             Arg Glu
                                  A       A               G   A

1081 CTGAACCCTGAGGCGGGGATGTGGCAGTGTCTGCTGAGTGACTCGGGACAGGTCCTGCTA
 336 Leu Asn Pro Glu Ala Gly Met Trp Gln Cys Leu Leu Ser Asp Ser Gly Gln Val Leu Leu

                                                                             G

     GAATCCAACATCAAGGTTGTGCCCACATGGCCCACCCCGGTGCAGCCAATGGCCCTGATT 1200
     Glu Ser Asn Ile Lys Val Val Pro Thr Trp Pro Thr Pro Val Gln Pro Met Ala Leu Ile 375
                             Leu             Ser
                             C               T                         - - - - - - - - -

1201 GTGCTGGGGGGCGTTGCGGGCCTCCTGCTTTTCACTGGGCTAGGCATCTTCTTCTGTGTC
 376 Val Leu Gly Gly Val Ala Gly Leu Leu Leu Phe Thr Gly Leu Gly Ile Phe Phe Cys Val
     - - - - - - - - - - - - - - - - - - - - - - - - - - - - - - - Ile - - - - - - - - - - - - - - - - -

                          C   C                                  T
```

```
                AGGTGCCGGCATCGAAGGCGTCAAGCAGAGCGGATGTCTCAGATCAAGAGACTCCTCAGT 1320
                Arg Cys Arg His Arg Arg Arg Gln Ala Glu Arg Met Ser Gln Ile Lys Arg Leu Leu Ser  415
                         C         C

  1321 GAAAAGAAGACCTGCCAGTGCCCTCACCGGTTTCAGAAGACATGTAGCCCCATTTGA 1377
   416 Glu Lys Lys Thr Cys Gln Cys Pro His Arg Phe Gln Lys Thr Cys Ser Pro Ile End  433
                A
```

Chimp CD4 Coding Sequence and Predicted Amino
Acid Sequence Showing Differences From Human
Sequences                                       15

```
     1 ATGAACCGGGGAGTCCCTTTTAGGCACTTGCTTCTGGTGCTGCAACTGGCACTCCTCCCA
   -25 Met Asn Arg Gly Val Pro Phe Arg His Leu Leu Leu Val Leu Gln Leu Ala Leu Leu Pro

                                                                            G
                              1
                              |
       GCAGCCACTCAGGGAAAGAAAGTGGTGCTGGGCAAGAAAGGGGACACAGTGGAACTGACC 120
       Ala Ala Thr Gln Gly Lys Lys Val Val Leu Gly Lys Lys Gly Asp Thr Val Glu Leu Thr  15
                                                           A        T

       *
   121 TGTACAGCTTCCCAGAAGAAGAGCATACAATTCCACTGGAAAAACTCCAACCAGACAAAG
    16 Cys Thr Ala Ser Gln Lys Lys Ser Ile Gln Phe His Trp Lys Asn Ser Asn Gln Thr Lys
                                                                                    Ile
                                                                                    T

       ATTCTGGGAAATCAGGGCTCCTTCTTAACTAAAGGTCCATCCAAGCTGAATGATCGCGTT 240
       Ile Leu Gly Asn Gln Gly Ser Phe Leu Thr Lys Gly Pro Ser Lys Leu Asn Asp Arg Val  55
                                                                                    Ala
                                                                                    C

   241 GACTCAAGAAGAAGCCTTTGGGACCAAGGAAACTTTACCCTGATCATCAAGAATCTTAAG
    56 Asp Ser Arg Arg Ser Leu Trp Asp Gln Gly Asn Phe Thr Leu Ile Ile Lys Asn Leu Lys
                                                  Pro
                                                  CC

                               *
       ATAGAAGACTCAGATACTTACATCTGTGAAGTGGGGGACCAGAAGGAGGAGGTGCAATTG 360
       Ile Glu Asp Ser Asp Thr Tyr Ile Cys Glu Val Gly Asp Gln Lys Glu Glu Val Gln Leu  95
                                                  Glu
                                                  A

   361 CTAGTGTTCGGATTGACTGCCAACTCTGACACCCACCTGCTTCAGGGGCAGAGCCTGACC
    96 Leu Val Phe Gly Leu Thr Ala Asn Ser Asp Thr His Leu Leu Gln Gly Gln Ser Leu Thr

                                                                   *
       CTGACCTTGGAGAGCCCCCCTGGTAGTAGCCCCTCAGTGCAATGTAGGAGTCCAAGGGGT 360
       Leu Thr Leu Glu Ser Pro Pro Gly Ser Ser Pro Ser Val Gln Cys Arg Ser Pro Arg Gly  135

   481 AAAAACATACAGGGGGGGAAGACCCTCTCCGTGTCTCAGCTGGAGCTCCAGGATAGTGGC
   136 Lys Asn Ile Gln Gly Gly Lys Thr Leu Ser Val Ser Gln Leu Glu Leu Gln Asp Ser Gly

            *
       ACCTGGACATGCACTGTCTTGCAGAACCAGAAGAAAGTGGAGTTCAAAATAGACATCGTG 600
       Thr Trp Thr Cys Thr Val Leu Gln Asn Gln Lys Lys Val Glu Phe Lys Ile Asp Ile Val  175
                                                                       G

   601 GTGCTAGCTTTCCAGAAGGCCTCCAGCATAGTCTATAAGAAAGAGGGGGAACAGGTGGAG
   176 Val Leu Ala Phe Gln Lys Ala Ser Ser Ile Val Tyr Lys Lys Glu Gly Glu Gln Val Glu

       TTCTCCTTCCCACTCGCCTTTACAGTTGAAAAGCTGACGGGCAGTGGCGAGCTGTGGTGG 720
       Phe Ser Phe Pro Leu Ala Phe Thr Val Glu Lys Leu Thr Gly Ser Gly Glu Leu Trp Trp  215
```

-continued

```
                                                      ---------
 721 CAGGCGGAGAGGGCTTCCTCCTCCAAGTCTTGGATCACCTTTGACCTGAAGAACAAGGAA
 216 Gln Ala Glu Arg Ala Ser Ser Ser Lys Ser Trp Ile Thr Phe Asp Leu Lys Asn Lys Glu

     GTGTCTGTAAAACGGGTTACCCAGGACCCTAAGCTCCAGATGGGCAAGAAGCTCCCGCTC  840
     Val Ser Val Lys Arg Val Thr Gln Asp Pro Lys Leu Gln Met Gly Lys Lys Leu Pro Leu  255

                                                      ---------
 841 CACCTCACCCTGCCCCAGGCCTTGCCTCAGTATGCTGGCTCTGGAAACCTCACCCTGGCC
 256 His Leu Thr Leu Pro Gln Ala Leu Pro Gln Tyr Ala Gly Ser Gly Asn Leu Thr Leu Ala

     CTTGAAGCGAAAACAGGAAAGTTGCATCAGGAAGTGAACCTCGTGGTGATGAGAGCCACT  840
     Leu Glu Ala Lys Thr Gly Lys Leu His Gln Glu Val Asn Leu Val Val Met Arg Ala Thr  295

                                                    G

             --------- *
 961 CAGCTCCAGAAAAATTTGACCTGTGAGGTGTGGGGACCCACCTCCCCTAAGCTGATGCTG
 296 Gln Leu Gln Lys Asn Leu Thr Cys Glu Val Trp Gly Pro Thr Ser Pro Lys Leu Met Leu

     AGCTTGAAACTGGAGAACAAGGAGGCAAAGGTCTCGAAGCGGGAGAAGGCGGTGTGGGTG  1080
     Ser Leu Lys Leu Glu Asn Lys Glu Ala Lys Val Ser Lys Arg Glu Lys Ala Val Trp Val  335

                                    *
1081 CTGAACCCTGAGGCGGGGATGTGGCAGTGTCTGCTGAGTGACTCGGGACAGGTCCTGCTG
 336 Leu Asn Pro Glu Ala Gly Met Trp Gln Cys Leu Leu Ser Asp Ser Gly Gln Val Leu Leu

     GAATCCAACATCAAGGTTCTGCCCACATGGTCCACCCCGGTGCAGCCAATGGCCCTGATT  1200
     Glu Ser Asn Ile Lys Val Leu Pro Thr Trp Ser Thr Pro Val Gln Pro Met Ala Leu Ile  375
                                                             ---------

1201 GTGCTGGGGGGCGTCGCCGGCCTCCTGCTTTTCATTGGGCTAGGCATCTTCTTCTGTGTC
 376 Val Leu Gly Gly Val Ala Gly Leu Leu Leu Phe Ile Gly Leu Gly Ile Phe Phe Cys Val
     ---------------------------------------------------------------------------

     AGGTGCCGGCACCGAAGGCGCCAAGCACAGCGGATGTCTCAGATCAAGAGACTCCTCAGT  1320
     Arg Cys Arg His Arg Arg Arg Gln Ala Gln Arg Met Ser Gln Ile Lys Arg Leu Leu Ser  415
                                         Glu
                                         G

1321 GAGAAGAAGACCTGCCAGTGCCCTCACCGGTTTCAGAAGACATGTAGCCCCATTTGA  1377
 416 Glu Lys Lys Thr Cys Gln Cys Pro His Arg Phe Gln Lys Thr Cys Ser Pro Ile End  433
```

The chimpanzee CD4 antigen is 99% homologous to its human counterpart, possessing 5 amino acid substitutions in the 433 amino acid predicted mature polypeptide, while the rhesus monkey CD4 is 92% homologous having 34 divergences from the human CD4 amino acid sequence. Antigen expression was effected transiently in CDM8 as well as stably using the retroviral vector pMNCS.

Example 2

Characterization of the Human CD4 Domain Which is Required For HIV Mediated Syncytium Formation These non-human primate CD4 antigens were expressed on human cells which were thereby rendered susceptible to infection by HIV, but formed strikingly fewer multinucleated giant cells, or syncytia, than their counterparts expressing the human CD4 antigen. Using in vitro mutagenesis this phenotype was localized to a single amino acid difference between the chimpanzee and human CD4 glycoproteins. This amino acid substitution quantitatively affects the ability of HeLa cells to form syncytia when these antigens are expressed in concert with the external and trans membrane proteins (EMP and TMP) of the human immunodeficiency virus type I (HIV). This was achieved by transiently expressing six trans-species hybrid CD4 antigens, which contain each of the three nonconservative extracellular amino acid sequence changes between the two species alone and in pairs, followed by infection with the Vaccinia:(HIV env) recombinant virus VSC25. The presence of a glycine residue at position 87, as found in chimpanzee CD4, instead of the glutamic acid residue found in human CD4, essentially eliminates the formation of multinucleated syncytia. Conversely the transfer of the human glutamic acid residue at position 87 to the chimpanzee CD4 confers the ability to form syncytia in the presence of HIV EMP and TMP. In contrast the absence or presence of either of the two amino acid substitutions which create glycosylation sites unique to the chimpanzee CD4 antigen, at amino acids 34 and 68 in the first immunoglobulin variable region homologous domain, has little or no effect on the extent of syncytium formed in this assay. We expect that all of these hybrid CD4 glycoproteins will show equal affinity for HIV EMP, since none of these amino acid sequence differences are in the HIV binding site defined earlier.

If syncytium formation is an important mechanism of HIV induced disease this blockade of HIV mediated syncytium formation may account for the resistance of the chimpanzee to the pathology of the acquired immune deficiency syndrome (AIDS) despite prolonged infection by HIV.

Example 3

Preparation of CD4-IG CDNA Constructs

The Extracellular portion of the chimpanzee or rhesus monkey coding sequence (encoding the signal peptides and amino acids 1-372 of the mature glycoproteins) is fused at three locations to a human IgG1 heavy chain constant region gene by means of a synthetic splice donor linker molecule. To exploit the splice donor linker, a BamHI linker having the sequence CGCGGATCCGCG is first inserted at amino acid residue 395 of the CD4 precursor sequence (nucleotide residue 1295). A synthetic splice donor sequence

GATCCCGAGGGTGAGTACTA

GGCTCCCACTCATGATTCGA bounded by BamHI and HindIII complementary ends is created and fused to the HindIII site in the intron preceding the CH1 domain, to the EspI site in the intron preceding the hinge domain, and to the BanI site preceding the CH2 domain of the IgG1 genomic sequence. Assembly of the chimeric genes by ligation at the BamHI site affords molecules in which either the variable (V) region, the V+CH1 regions, or the V, CH1 and hinge regions are replaced by CD4. In the last case, the chimeric molecule is expected to form a monomer structure, while in the former, a dimeric molecule is expected.

Immunoprecipitation of the fusion proteins with a panel of monoclonal antibodies directed against CD4 epitopes will show that all of the epitopes are preserved. A specific high affinity association is demonstrated between the chimeric molecules and HIV envelope proteins expressed on the surface of cells transfected with an attenuated (reverse transcriptase deleted) proviral construct, or infected with a vaccinia:HIV env recombinant virus.

Example 4

Preparation of the Fusion Proteins from Supernatants of COS Cells

COS cells grown in DME medium supplemented with 10% Calf Serum and gentamicin sulfate at 15 μg/ml are split into DME medium containing 10% NuSerum (Collaborative Research) and gentamicin to give 50% confluence the day before transfection. The next day, CsCl purified plasmid DNA is added to a final concentration of 0.1 to 2.0 μg/ml followed by DEAE Dextran to 400 μg/ml and chloroquine to 100 μM. After 4 hours at 37° C., the medium is aspirated and a 10% solution of dimethyl sulfoxide in phosphate buffered saline is added for 2 minutes, aspirated, and replaced with DME/10% Calf Serum. 8 to 24 hours later, the cells are trypsinized and split 1:2.

For radiolabeling, the medium is aspirated 40 to 48 hours after transfection, the cells are washed once with phosphate buffered saline, and DME medium lacking cysteine or methionine is added. 30 minutes later, $^{35}S$-labeled cysteine and methionine are added to final concentrations of 30–60 μci and 100–200 μci respectively, and the cells allowed to incorporate label for 8 to 24 more hours. The supernatants are recovered and examined by electrophoresis on 7.5% polyacrylamide gels following denaturation and reduction, or on 5% polyacrylamide following denaturation without reduction. The IgG-CD4 fusion proteins form dimer structures. The CD4-IgM fusion proteins form large multimers beyond the resolution of the gel system without reduction, and monomers of the expected molecular mass with reduction.

Unlabeled proteins are prepared by allowing the cells to grow for 5 to 10 days post transfection in DME medium containing 5% NuSerum and gentamicin as above. The supernatants are harvested, centrifuged, and purified by batch adsorption to either protein A trisacryl, protein A agarose, goat anti-human IgG antibody agarose, rabbit anti-human IgM antibody agarose, or monoclonal anti-CD4 antibody agarose. Antibody agarose conjugates are prepared by coupling purified antibodies to cyanogen bromide activated agarose according to the manufacturer's recommendations, and using an antibody concentration of 1 mg/ml. Following batch adsorption by shaking overnight on a rotary table, the beads are harvested by pouring into a sintered glass funnel and washed a few times on the funnel with phosphate buffered saline containing 1% Nonidet P40 detergent. The beads are removed from the funnel and poured into a small disposable plastic column (Quik-Sep QS-Q column, Isolab), washed with at least 20 column volumes of phosphate buffered saline containing 1% Nonidet P40, with 5 volumes of 0.15M NaCl, 1 mM EDTA (pH 8.0), and eluted by the addition of either 0.1M acetic acid, 0.1M acetic acid containing 0.1M NaCl, or 0.25M glycine-HCl buffer, pH 2.5.

Example 5

Blockage of Syncytium Formation by the Fusion Proteins

Purified or partially purified fusion proteins are added to HPB-ALL cells infected 12 hours previously with a vaccinia virus recombinant encoding HIV envelope protein. After incubation for 6–8 more hours, the cells are washed with phosphate buffered saline, fixed with formaldehyde, and photographed. All of the full-length CD4 immunoglobulin fusion proteins will show inhibition of syncytium formation.

Having now fully described this invention, it will be appreciated by those skilled in the art that the same can be performed with any wide range of equivalent parameters of composition, conditions, and methods of preparing such recombinant molecules, vectors, transformed hosts and proteins without departing from the spirit or scope of the invention or any embodiment thereof.

What is claimed is:

1. An isolated polynucleotide molecule coding for rhesus monkey CD4 and having the following DNA sequence:

```
  1 ATGAACCGGGGAATCCCTTTTAGGCACTTG
-25 Met Asn Arg Gly Ile Pro Phe Arg His Leu

    CTTCTGGTGCTGCAACTGGCGCTACTCCCA
    Leu Leu Val Leu Gln Leu Ala Leu Leu Pro

    GCAGTCACCCAGGGAAAGAAAGTGGTGCTG
    Ala Val Thr Gln Gly Lys Lys Val Val Leu

    GGCAAGAAAGGGGATACAGTGGAACTGACC  120
    Gly Lys Lys Gly Asp Thr Val Glu Leu Thr  15
```

-continued

121 TGTACAGCTTCGCAGAAGAACACACAA
16 Cys Thr Ala Ser Gln Lys Asn Thr Gln

TTCCACTGGAAAAACTCCAACCAGATAAAG
Phe His Trp Lys Asn Ser Asn Gln Ile Lys

ATTCTGGGAATTCAGGGTCTCTTCTTAACT
Ile Leu Gly Ile Gln Gly Leu Phe Leu Thr

AAAGGTCCATCCAAGCTGAGCGATCGTGCT 240
Lys Gly Pro Ser Lys Leu Ser Asp Arg Ala 55

241 GACTCAAGAAAAAGCCTTTGGGACCAAGGA
56 Asp Ser Arg Lys Ser Leu Trp Asp Gln Gly

TGCTTTTCCATGATCATCAAGAATCTTAAG
Cys Phe Ser Met Ile Ile Lys Asn Leu Lys

ATAGAAGACTCAGATACTTACATCTGTGAA
Ile Glu Asp Ser Asp Thr Tyr Ile Cys Glu

GTGGAGAACAAGAAGGAGGAGGTGGAATTG 360
Val Glu Asn Lys Lys Glu Glu Val Glu Leu 95

361 CTGGTGTTCGGATTGACTGCCAACTCTGAC
96 Leu Val Phe Gly Leu Thr Ala Asn Ser Asp

ACCCACCTGCTTGAGGGGCAAAGCCTGACC
Thr His Leu Leu Glu Gly Gln Ser Leu Thr

CTGACCTTGGAGAGCCCCCCTGGTAGTAGC
Leu Thr Leu Glu Ser Pro Pro Gly Ser Ser

CCCTCAGTGAAATGTAGGAGTCCAGGGGGT 480
Pro Ser Val Lys Cys Arg Ser Pro Gly Gly 135

481 AAAAACATACAGGGGGGGAGGACCATCTCT
136 Lys Asn Ile Gln Gly Gly Arg Thr Ile Ser

GTGCCTCAGCTGGAGCGCCAGGATAGTGGC
Val Pro Gln Leu Glu Arg Gln Asp Ser Gly

ACCTGGACATGCACCGTCTCGCAGGACCAG
Thr Trp Thr Cys Thr Val Ser Gln Asp Gln

AAGACGGTGGAGTTCAAAATAGACATCGTG 600
Lys Thr Val Glu Phe Lys Ile Asp Ile Val 175

601 GTGCTAGCTTTCCAGAAGGCCTCCAGCACA
176 Val Leu Ala Phe Gln Lys Ala Ser Ser Thr

GTCTATAAGAAAGAGGGGGAACAGGTGGAG
Val Tyr Lys Lys Glu Gly Glu Gln Val Glu

TTCTCCTTCCCACTCGCCTTTACACTTGAA
Phe Ser Phe Pro Leu Ala Phe Thr Leu Glu

AAGCTGACGGGCAGTGGCGAGCTGTGGTGG 720
Lys Leu Thr Gly Ser Gly Glu Leu Trp Trp 215

-continued

721 CAGGCGGAGAGGGCCTCCTCCTCCAAGTCT
216 Gln Ala Glu Arg Ala Ser Ser Ser Lys Ser

TGGATTACCTTCGACCTGAAGAACAAGGAA
Trp Ile Thr Phe Asp Leu Lys Asn Lys Glu

GTGTCTGTAAAACGGGTTACCCAGGACCCC
Val Ser Val Lys Arg Val Thr Gln Asp Pro

AAGCTCCAGATGGGCAAGAAGCTCCCGCTC 840
Lys Leu Gln Met Gly Lys Lys Leu Pro Leu 255

841 CACCTCACCCTGCCCCAGGCCTTGCCTCAG
256 His Leu Thr Leu Pro Gln Ala Leu Pro Gln

TATGCTGGCTCTGGAAACCTCACGCTGGCC
Tyr Ala Gly Ser Gly Asn Leu Thr Leu Ala

CTTGAAGCGAAAACAGGAAAGTTGCATCAG
Leu Glu Ala Lys Thr Gly Lys Leu His Gln

GAAGTGAACCTCGTGGTGATGAGAGCCACT 960
Glu Val Asn Leu Val Val Met Arg Ala Thr 295

961 CAGTTCCAGGAAAATTTGACCTGTGAAGTG
296 Gln Phe Gln Glu Asn Leu Thr Cys Glu Val

TGGGGACCCACCTCCCCTAAGCTGACGCTG
Trp Gly Pro Thr Ser Pro Lys Leu Thr Leu

AGCTTGAAACTGGAGAACAAGGGGGCAACG
Ser Leu Lys Leu Glu Asn Lys Gly Ala Thr

GTCTCGAAGCAGGCGAAGGCGGTGTGGGTG 1080
Val Ser Lys Gln Ala Lys Ala Val Trp Val 335

1081 CTGAACCCTGAGGCGGGGATGTGGCAGTGT
336 Leu Asn Pro Glu Ala Gly Met Trp Gln Cys

CTGCTGAGTGACTCGGGACAGGTCCTGCTA
Leu Leu Ser Asp Ser Gly Gln Val Leu Leu

GAATCCAACATCAAGGTTGTGCCCACATGG
Glu Ser Asn Ile Lys Val Val Pro Thr Trp

CCCACCCCGGTGCAGCCAATGGCCCTGATT 1200
Pro Thr Pro Val Gln Pro Met Ala Leu Ile 375

1201 GTGCTGGGGGGCGTTGCGGGCCTCCTGCTT
376 Val Leu Gly Gly Val Ala Gly Leu Leu Leu

TTCACTGGGCTAGGCATCTTCTTCTGTGTC
Phe Thr Gly Leu Gly Ile Phe Phe Cys Val

AGGTGCCGGCATCGAAGGCGTCAAGCAGAG
Arg Cys Arg His Arg Arg Arg Gln Ala Glu

CGGATGTCTCAGATCAAGAGACTCCTCAGT 1320
Arg Met Ser Gln Ile Lys Arg Leu Leu Ser 415

-continued

1321 GAAAAGAAGACCTGCCAGTGCCCTCACCGG
416 Glu Lys Lys Thr Cys Gln Cys Pro His Arg

TTTCAGAAGACATGTAGCCCCATT
Phe Gln Lys Thr Cys Ser Pro Ile ;

or a degenerative variant thereof.

2. The isolated polynucleotide molecule according to claim 1 having the following DNA sequence:

| | | |
|---|---|---|
| 1<br>−25 | ATGAACCGGGGAATCCCTTTTAGGCACTTGCTTCTGGTGCTGCAACTGGCGCTACTCCCA<br>Met Asn Arg Gly Ile Pro Phe Arg His Leu Leu Leu Val Leu Gln Leu Ala Leu Leu Pro | |
| | GCAGTCACCCAGGGAAAGAAAGTGGTGCTGGGCAAGAAAGGGGATACAGTGGAACTGACC<br>Ala Val Thr Gln Gly Lys Lys Val Val Leu Gly Lys Lys Gly Asp Thr Val Glu Leu Thr | 120<br>15 |
| 121<br>16 | TGTACAGCTTCGCAGAAGAAGAACACACAATTCCACTGGAAAAACTCCAACCAGATAAAG<br>Cys Thr Ala Ser Gln Lys Lys Asn Thr Gln Phe His Trp Lys Asn Ser Asn Gln Ile Lys | |
| | ATTCTGGGAATTCAGGGTCTCTTCTTAACTAAAGGTCCATCCAAGCTGAGCGATCGTGCT<br>Ile Leu Gly Ile Gln Gly Leu Phe Leu Thr Lys Gly Pro Ser Lys Leu Ser Asp Arg Ala | 240<br>55 |
| 241<br>56 | GACTCAAGAAAAAGCCTTTGGGACCAAGGATGCTTTTCCATGATCATCAAGAATCTTAAG<br>Asp Ser Arg Lys Ser Leu Trp Asp Gln Gly Cys Phe Ser Met Ile Ile Lys Asn Leu Lys | |
| | ATAGAAGACTCAGATACTTACATCTGTGAAGTGGAGAACAAGAAGGAGGAGGTGGAATTG<br>Ile Glu Asp Ser Asp Thr Tyr Ile Cys Glu Val Glu Asn Lys Lys Glu Glu Val Glu Leu | 360<br>95 |
| 361<br>96 | CTGGTGTTCGGATTGACTGCCAACTCTGACACCCACCTGCTTGAGGGGCAAAGCCTGACC<br>Leu Val Phe Gly Leu Thr Ala Asn Ser Asp Thr His Leu Leu Glu Gly Gln Ser Leu Thr | |
| | CTGACCTTGGAGAGCCCCCCTGGTAGTAGCCCCTCAGTGAAATGTAGGAGTCCAGGGGGT<br>Leu Thr Leu Glu Ser Pro Pro Gly Ser Ser Pro Ser Val Lys Cys Arg Ser Pro Gly Gly | 480<br>135 |
| 481<br>136 | AAAAACATACAGGGGGGGAGGACCATCTCTGTGCCTCAGCTGGAGCGCCAGGATAGTGGC<br>Lys Asn Ile Gln Gly Gly Arg Thr Ile Ser Val Pro Gln Leu Glu Arg Gln Asp Ser Gly | |
| | ACCTGGACATGCACCGTCTCGCAGGACCAGAAGACGGTGGAGTTCAAAATAGACATCGTG<br>Thr Trp Thr Cys Thr Val Ser Gln Asp Gln Lys Thr Val Glu Phe Lys Ile Asp Ile Val | 600<br>175 |
| 601<br>176 | GTGCTAGCTTTCCAGAAGGCCTCCAGCACAGTCTATAAGAAAGAGGGGGAACAGGTGGAG<br>Val Leu Ala Phe Gln Lys Ala Ser Ser Thr Val Tyr Lys Lys Glu Gly Glu Gln Val Glu | |
| | TTCTCCTTCCCACTCGCCTTTACACTTGAAAAGCTGACGGGCAGTGGCGAGCTGTGGTGG<br>Phe Ser Phe Pro Leu Ala Phe Thr Leu Glu Lys Leu Thr Gly Ser Gly Glu Leu Trp Trp | 720<br>215 |
| 721<br>216 | CAGGCGGAGAGGGCCTCCTCCTCCAAGTCTTGGATTACCTTCGACCTGAAGAACAAGGAA<br>Gln Ala Glu Arg Ala Ser Ser Ser Lys Ser Trp Ile Thr Phe Asp Leu Lys Asn Lys Glu | |
| | GTGTCTGTAAAACGGGTTACCCAGGACCCCAAGCTCCAGATGGGCAAGAAGCTCCCGCTC<br>Val Ser Val Lys Arg Val Thr Gln Asp Pro Lys Leu Gln Met Gly Lys Lys Leu Pro Leu | 840<br>255 |
| 841<br>256 | CACCTCACCCTGCCCCAGGCCTTGCCTCAGTATGCTGGCTCTGGAAACCTCACGCTGGCC<br>His Leu Thr Leu Pro Gln Ala Leu Pro Gln Tyr Ala Gly Ser Gly Asn Leu Thr Leu Ala | |
| | CTTGAAGCGAAAACAGGAAAGTTGCATCAGGAAGTGAACCTCGTGGTGATGAGAGCCACT<br>Leu Glu Ala Lys Thr Gly Lys Leu His Gln Glu Val Asn Leu Val Val Met Arg Ala Thr | 960<br>295 |
| 961<br>296 | CAGTTCCAGGAAAATTTGACCTGTGAAGTGTGGGGACCCACCTCCCCTAAGCTGACGCTG<br>Gln Phe Gln Glu Asn Leu Thr Cys Glu Val Trp Gly Pro Thr Ser Pro Lys Leu Thr Leu | |
| | AGCTTGAAACTGGAGAACAAGGGGGCAACGGTCTCGAAGCAGGCGAAGGCGGTGTGGGTG<br>Ser Leu Lys Leu Glu Asn Lys Gly Ala Thr Val Ser Lys Gln Ala Lys Ala Val Trp Val | 1080<br>335 |
| 1081<br>336 | CTGAACCCTGAGGCGGGGATGTGGCAGTGTCTGCTGAGTGACTCGGGACAGGTCCTGCTA<br>Leu Asn Pro Glu Ala Gly Met Trp Gln Cys Leu Leu Ser Asp Ser Gly Gln Val Leu Leu | |
| | GAATCCAACATCAAGGTTGTGCCCACATGGCCCACCCCGGTGCAGCCAATGGCCCTGATT<br>Glu Ser Asn Ile Lys Val Val Pro Thr Trp Pro Thr Pro Val Gln Pro Met Ala Leu Ile | 1200<br>375 |
| 1201<br>376 | GTGCTGGGGGGCGTT,CGGGCCTCCTGCTTTTCACTGGGCTAGGCATCTTCTTCTGTGTC<br>Val Leu Gly Gly Val Ala Gly Leu Leu Leu Phe Thr Gly Leu Gly Ile Phe Phe Cys Val | |
| | AG,TGCCGGCATCGAAGGCGTCAAGCAGAGCGGATGTCTCAGATCAAGAGACTCCTCAGT<br>Arg Cys Arg His Arg Arg Arg Gln Ala Glu Arg Met Ser Gln Ile Lys Arg Leu Leu Ser | 1320<br>415 |
| 1321<br>416 | GAAAAGAAGACCTGCCAGTGCCCTCACCGGTTTCAGAAGACATGTAGCCCCATT<br>Glu Lys Lys Thr Cys Gln Cys Pro His Arg Phe Gln Lys Thr Cys Ser Pro Ile. | |

3. An isolated polynucleotide molecule coding for a rhesus monkey CD4 fragment and having the following DNA sequence:

1 ATGAACCGGGGAATCCCTTTTAGGCACTTGCTTCTGGTGCTGCAACTGGCGCTACTCCCA
−25 Met Asn Arg Gly Ile Pro Phe Arg His Leu Leu Leu Val Leu Gln Leu Ala Leu Leu Pro

GCAGTCACCCAGGGAAAGAAAGTGGTGCTGGGCAAGAAAGGGGATACAGTGGAACTGACC 120
Ala Val Thr Gln Gly Lys Lys Val Val Leu Gly Lys Lys Gly Asp Thr Val Glu Leu Thr 15

121 TGTACAGCTTCGCAGAAGAAGAACACACAATTCCACTGGAAAAACTCCAACCAGATAAAG
16 Cys Thr Ala Ser Gln Lys Lys Asn Thr Gln Phe His Trp Lys Asn Ser Asn Gln Ile Lys

ATTCTGGGAATTCAGGGTCTCTTCTTAACTAAAGGTCCATCCAAGCTGAGCGATCGTGCT 240
Ile Leu Gly Ile Gln Gly Leu Phe Leu Thr Lys Gly Pro Ser Lys Leu Ser Asp Arg Ala 55

241 GACTCAAGAAAAAGCCTTTGGGACCAAGGATGCTTTTCCATGATCATCAAGAATCTTAAG
56 Asp Ser Arg Lys Ser Leu Trp Asp Gln Gly Cys Phe Ser Met Ile Ile Lys Asn Leu Lys

ATAGAAGACTCAGATACTTACATCTGTGAAGTGGAGAACAAGAAGGAGGAGGTGGAATTG 360
Ile Glu Asp Ser Asp Thr Tyr Ile Cys Glu Val Glu Asn Lys Lys Glu Glu Val Glu Leu 95

361 CTGGTGTTCGGATTGACTGCCAACTCTGACACCCACCTGCTT
96 Leu Val Phe Gly Leu Thr Ala Asn Ser Asp Thr His Leu Leu;

or a degenerate variant thereof.

4. The isolated polynucleotide molecule according to claim 3 having the following DNA sequence:

1 ATGAACCGGGGAATCCCTTTTAGGCACTTGCTTCTGGTGCTGCAACTGGCGCTACTCCCA
−25 Met Asn Arg Gly Ile Pro Phe Arg His Leu Leu Leu Val Leu Gln Leu Ala Leu Leu Pro

GCAGTCACCCAGGGAAAGAAAGTGGTGCTGGGCAAGAAAGGGGATACAGTGGAACTGACC 120
Ala Val Thr Gln Gly Lys Lys Val Val Leu Gly Lys Lys Gly Asp Thr Val Glu Leu Thr 15

121 TGTACAGCTTCGCAGAAGAAGAACACACAATTCCACTGGAAAAACTCCAACCAGATAAAG
16 Cys Thr Ala Ser Gln Lys Lys Asn Thr Gln Phe His Trp Lys Asn Ser Asn Gln Ile Lys

ATTCTGGGAATTCAGGGTCTCTTCTTAACTAAAGGTCCATCCAAGCTGAGCGATCGTGCT 240
Ile Leu Gly Ile Gln Gly Leu Phe Leu Thr Lys Gly Pro Ser Lys Leu Ser Asp Arg Ala 55

241 GACTCAAGAAAAAGCCTTTGGGACCAAGGATGCTTTTCCATGATCATCAAGAATCTTAAG
56 Asp Ser Arg Lys Ser Leu Trp Asp Gln Gly Cys Phe Ser Met Ile Ile Lys Asn Leu Lys

ATAGAAGACTCAGATACTTACATCTGTGAAGTGGAGAACAAGAAGGAGGAGGTGGAATTG 360
Ile Glu Asp Ser Asp Thr Tyr Ile Cys Glu Val Glu Asn Lys Lys Glu Glu Val Glu Leu 95

361 CTGGTGTTCGGATTGACTGCCAACTCTGACACCCACCTGCTT
96 Leu Val Phe Gly Leu Thr Ala Asn Ser Asp Thr His Leu Leu

5. A polynucleotide molecule specifying a fusion protein, having:

1) the polynucleotide molecule according to any one of claims 1, 2, 3, or 4 linked to 2) a polynucleotide molecule encoding a cytotoxic polypeptide.

6. A vector comprising the polynucleotide molecule of any one of claims 1, 2, 3 or 4.

7. A bacterial or eukaryotic host cell transformed with the vector of claim 6.

* * * * *